(12) United States Patent
Curran et al.

(10) Patent No.: US 9,597,408 B2
(45) Date of Patent: Mar. 21, 2017

(54) PEPTIDE-MEDIATED NON-COVALENT DELIVERY OF ACTIVE AGENTS ACROSS THE BLOOD-BRAIN BARRIER

(71) Applicant: Mayo Foundation for Medical Education and Research, Rochester, MN (US)

(72) Inventors: Geoffry L. Curran, Rochester, MN (US); Gobinda Sarkar, Rochester, MN (US); Joseph F. Poduslo, Zumbro Falls, MN (US); Robert B. Jenkins, Rochester, MN (US); Val J. Lowe, Rochester, MN (US); Erik W. Mahlum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 106 days.

(21) Appl. No.: 14/281,389

(22) Filed: May 19, 2014

(65) Prior Publication Data
US 2014/0328866 A1   Nov. 6, 2014

Related U.S. Application Data

(62) Division of application No. 13/383,710, filed as application No. PCT/US2010/041924 on Jul. 14, 2010, now abandoned.

(60) Provisional application No. 61/225,412, filed on Jul. 14, 2009.

(51) Int. Cl.
| A61K 38/16 | (2006.01) |
| A61K 47/48 | (2006.01) |
| A61K 51/12 | (2006.01) |
| C07K 14/775 | (2006.01) |
| A61K 38/47 | (2006.01) |
| A61K 39/395 | (2006.01) |

(52) U.S. Cl.
CPC ........ *A61K 47/48246* (2013.01); *A61K 38/47* (2013.01); *A61K 39/39533* (2013.01); *A61K 51/12* (2013.01); *C07K 14/775* (2013.01)

(58) Field of Classification Search
None
See application file for complete search history.

(56) References Cited

U.S. PATENT DOCUMENTS

| 4,647,447 | A  | 3/1987  | Gries et al. |
| 5,168,045 | A  | 12/1992 | Dyer et al. |
| 5,591,721 | A  | 1/1997  | Agrawal et al. |
| 5,652,356 | A  | 7/1997  | Agrawal |
| 6,245,751 | B1 | 6/2001  | Crutcher et al. |
| 6,509,154 | B1 | 1/2003  | de Paillette |
| 8,877,726 | B2 | 11/2014 | Kreutzer et al. |
| 2002/0173456 | A1 | 11/2002 | Smith et al. |
| 2004/0229219 | A1 | 11/2004 | Gallaher et al. |
| 2004/0241164 | A1* | 12/2004 | Bales et al. ............... 424/145.1 |
| 2006/0198833 | A1 | 9/2006  | Verma et al. |
| 2007/0086981 | A1 | 4/2007  | Meijer et al. |
| 2008/0213185 | A1 | 9/2008  | Hong et al. |
| 2010/0119528 | A1 | 5/2010  | Sarkar et al. |
| 2014/0314663 | A1 | 10/2014 | Sarkar et al. |

FOREIGN PATENT DOCUMENTS

| WO | WO 99/07409  | 2/1999 |
| WO | WO 99/32619  | 7/1999 |
| WO | WO 00/01846  | 1/2000 |
| WO | WO 00/44895  | 8/2000 |
| WO | WO 00/44914  | 8/2000 |
| WO | WO 01/29058  | 4/2001 |
| WO | WO 01/36646  | 5/2001 |
| WO | WO 2011/008823 | 1/2011 |

OTHER PUBLICATIONS

P02649 entry in UniProt (retrieved from http://www.uniprot.org/uniprot/P02649 on Apr. 27, 2015, 16 pages).*
Vuilleumier et al ('Autoantibodies to apolipoprotein A-1 as a biomarker of cardiovascular autoimmunity' World J Cardiol May 26 2014 v6(5) pp. 314-326, printed as a total of 14 pages).*
Authorized Officer J. H. Kim. International Search Report and Written Opinion in International Application No. PCT/US2010/041924, mailed Mar. 24, 2011, 13 pages.
Authorized Officer N. Lindner. International Preliminary Report on Patentability in International Application No. PCT/US2010/041924, mailed Jan. 17, 2012, 8 pages.
Abbott et al., "PMID: 16371949 Astrocyte-endothelial interactions at the blood-brain barrier," *Nat Rev Neurosci*, 2006, 7(1):41-53.
Bacher et al., "Peripheral and central biodistribution of (111)In-labeled anti-beta-amyloid autoantibodies in a transgenic mouse model of Alzheimer's disease," *Neurosci Lett.*, 2009, 449(3):240-5.
Ballantyne, "Peptide YY(1-36) and Peptide YY(3-36): Part I. Distribution, Release and Actions," *Obesity Surgery*, 2006, 16(5):651-658.
Bass, "RNA interference: The short answer," *Nature*, 2001, 411:428-429.
Boado et al., "Drug targeting of erythropoietin across the primate blood-brain barrier with an IgG molecular Trojan horse," *J Pharmacol Exp Ther.*, 2010, 333(3):961-9.
Brown and Goldstein, "A receptor-mediated pathway for cholesterol homeostasis," *Science*, 1986, 232(4746):34-47.
Chenna et al., "Multiple sequence alignment with the Clustal series of programs," *Nucleic Acids Res.*, 2003, 31(13):3497-3500.

(Continued)

*Primary Examiner* — Karlheinz R Skowronek
*Assistant Examiner* — Ronald Niebauer
(74) *Attorney, Agent, or Firm* — Fish & Richardson, P.C.

(57) ABSTRACT

The peptides described herein can function as carrier peptides. These peptides can associate with (e.g., non-covalently bind) biologically active molecules or imaging agents to transport the biologically active molecules or imaging across the blood-brain barrier. In some cases, such transport may increase the effectiveness of the biological molecules or imaging agents.

2 Claims, 9 Drawing Sheets

(56) References Cited

OTHER PUBLICATIONS

De Boer and Breimer, "The blood-brain barrier: clinical implications for drug delivery to the brain," *J R Coll Physicians Lond*, 1994, 28(6):502-6.
Deane et al., "IgG-assisted age-dependent clearance of Alzheimer's amyloid beta peptide by the blood-brain barrier neonatal Fc receptor," *J. Neurosci.*, 2005, 25:11495-11503.
Deeken and Löscher, "The blood-brain barrier and cancer: transporters, treatment, and Trojan horses," *Clin Cancer Res.*, 2007, 13(6):1663-74.
Denora et al., "Recent advances in medicinal chemistry and pharmaceutical technology—strategies for drug delivery to the brain," *Curr Top Med Chem*, 2009, 9(2):182-96.
Dietz and Bähr, "Delivery of bioactive molecules into the cell: the Trojan horse approach," *Mol Cell Neurosci.*, 2004, 27(2):85-131.
Egholm et al., "PNA hybridizes to complementary oligonucleotides obeying the Watson-Crick hydrogen-bonding rules," *Nature*, 1993, 365, 566.
Elbashir et al., "Duplexes of 21-nucleotide RNAs mediate RNA interference in cultured mammalian cells," *Nature*, 2001, 411:494-498.
Friden et al., "Blood-brain barrier penetration and in vivo activity of an NGF conjugate," *Science*, 1993, 259(5093):373-7.
Hawkins and Davis, "The blood-brain barrier/neurovascular unit in health and disease," *Pharmacol Rev.*, 2005, 57(2):173-85.
Holcomb et al., "Accelerated Alzheimer-type phenotype in transgenic mice carrying both mutant amyloid precursor protein and presenilin 1 transgenes," *Nat Med.*, 1998, 4(1):97-100.
Hulsermann et al., "Uptake of apolipoprotein E fragment coupled liposomes by cultured brain microvessel endothelial cells and intact brain capillaries," *J Drug Target*, 2009, 17(8):610-618.
Hussain et al., "The mammalian low-density lipoprotein receptor family," *Annu Rev Nutr.*, 1999, 19:141-72.
Jefferies et al., "Transferrin receptor on endothelium of brain capillaries," *Nature*, 1984, 312:162-163.
Karkan et al., "A unique carrier for delivery of therapeutic compounds beyond the blood-brain barrier," *PLoS One*, 2008, (6):e2469.
Kim et al., "Translocation of poly(ethylene glycol-co-hexadecyl)cyanoacrylate nanoparticles into rate brain endothelial cells: role of apolipoproteins in receptor-mediated endocytosis," *Biomacromolecules*, 2007, 8(3):793-799.
Kreuter et al., "Apolipoprotein-mediated transport of nanoparticle-bound drugs across the blood-brain barrier," *J Drug Target*, 2002, 10(4):317-325.
Leupold et al., "Apolipoprotein E peptide-modified colloidal carriers: The design determines the mechanism of uptake in vascular endothelial cells," *Biochim Biophys Acta*, 2009, 1788:442-449.
Mahlum et al., "Engineering a noncarrier to a highly efficient carrier peptide for noncovalently delivering biologically active proteins into human cells," *Anal Biochem.*, 2007, 365(2):215-21.
Mazza et al., "Cancer and the blood-brain barrier: 'Trojan horses' for courses?" *Br J Pharmacol.*, 2008, 155(2):149-51.
Michaelis et al., "Covalent Linkage of Apolipoprotein E to Albumin Nanoparticles Strongly Enhances Drug Transport into the Brain," *J of Pharmacology & Experimental Therapeutics*, 2006, 317(3):1246-1253.
Misra et al., "Drug delivery to the central nervous system: a review," *J Pharm Pharm Sci.*, 2003, 6(2):252-73.
Morris et al., "A peptide carrier for the delivery of biologically active proteins into mammalian cells," *Nat Biotechnol*, 2001, 19(12):1173-6.
Mousazahed et al., "Gene delivery to brain cells with apoprotein E derived peptide conjugated to polylysine (apoEdp-PLL)," *J of Drug Target*, 2007, 15(3):226-230.
Pan et al., "Efficient transfer of receptor-associated protein (RAP) across the blood-brain barrier," *J Cell Sci.*, 2004, 117(Pt 21):5071-8.
Pardridge, "Blood-brain barrier delivery," *Drug Discov Today*, 2007,12(1-2):54-61.

Pardridge, "Re-engineering biopharmaceuticals for delivery to brain with molecular Trojan horses," *Bioconjug Chem.*, 2008, 19(7):1327-38.
Patel et al., "Getting into the brain: approaches to enhance brain drug delivery," *CNS Drugs*, 2009, 23(1):35-58.
Persidsky et al., "Blood-brain barrier: structural components and function under physiologic and pathologic conditions," *J Neuroimmune Pharmacol.*, 2006, 1(3):223-36.
Poduslo et al., "Permeability of proteins at the blood-brain barrier in the normal adult mouse and double transgenic mouse model of Alzheimer's disease," *Neurobiol Dis.*, 2001, 8(4):555-67.
Ramakrishnan et al., "Surface plasmon resonance binding kinetics of Alzheimer's disease amyloid beta peptide-capturing and plaque-binding monoclonal antibodies," *Biochemistry*, 2009, 48(43):10405-15.
Ruan et al., "Cytokine regulation of low-density lipoprotein receptor gene transcription in human mesangial cells," *Nephrol Dial Transplant*, 1998, 13(6):1391-7.
Sarkar et al. "A Carrier for non-covalent delivery of functional beta-galactosidase and antibodies against amyloid plaques and igm to the brain," *PLoS One*, 2011, 6(12):e28881.
Sauer et al., "An Apolipoprotein E-Derived Peptide Mediates Uptake of Sterically Stabilized Liposomes into Brain Capillary Endothelial Cells," *Biochem*, 2005, 44:2021-2029.
Schwarze et al., "In vivo protein transduction: delivery of a biologically active protein into the mouse," *Science*, 1999, 285(5433):1569-72.
Shamenkov et al., "Effects of apolipoproteins on dalargin transport across the blood-brain barrier," *Bull Exp Biol Med*, 2006, 142(6):703-706.
Spencer and Verma, "Targeted delivery of proteins across the blood-brain barrier," *Proc Natl Acad. Sci U S A*, 2007, 104(18):7594-9.
Stein and Cheng, "Antisense oligonucleotides as therapeutic agents—is the bullet really magical?" *Science*, 1993, 261:1004.
Weiss et al., "The blood-brain barrier in brain homeostasis and neurological diseases," *Biochim Biophys Acta*, 2009, 1788(4):842-57.
Wengenack et al., "Targeting alzheimer amyloid plaques in vivo," *Nat Biotechnol*, 2000, 18(8):868-72
Zensi et al., "Albumin nanoparticles targeted with Apo E enter the CNS by transcytosis and are delivered to neurones," *J of Controlled Release*, 2009, 137:78-86.
Zlokovic et al., "Differential regulation of leptin transport by the choroid plexus and blood-brain barrier and high affinity transport systems for entry into hypothalamus and across the blood-cerebrospinal fluid barrier," *Endocrinology*, 2000, 141:1434-1441.
Zlokovic, "The blood-brain barrier in health and chronic neurodegenerative disorders," *Neuron*, 2008, 57(2):178-201.
Rall, Structural basis for receptor binding heterogeneity of apolipoprotein E from type III hyperlipoproteinemic subjects, Proc. Natl. Acad. Sci. USA 79: 4696-4700, 1982.
Fagan et al ('Apolipoprotein E-containing high density lipoprotein promotes neurite outgrowth and is a ligand for the low density lipoprotein receptor-related protein JBC v271(47) Nov. 1996 pp. 30121-30125).
Addgene vector information (retrieved from http://www.addgene.org/vector-database/2544/ on Jan. 28, 2014, 3 pages).
NCBI abstract (retrieved from http://www.ncbi.nlm.nih.gov/pubmed/19694613 on Jan. 28, 2014, 2 pages).
Abraham, "The factors that influence permeation across the blood-brain barrier," *Eur J Med Chem.*, 39(3):235-240, Mar. 2004.
Ansel, "Introduction to Pharmaceutical Dosage Forms," Fourth Edition 1985, 126.
Blanchette and Fortin, "Blood-brain barrier disruption in the treatment of brain tumors," *Methods Mol Biol.*, 686:447-463, 2011.
Choi et al., "Microbubble-size dependence of focused ultrasound-induced blood-brain barrier opening in mice in vivo," *IEEE Trans Biomed Eng.*, 57(1):145-154, Epub Oct. 20, 2009.
Cosolo et al., "Blood-brain barrier disruption using mannitol: time course and electron microscopy studies," *Am J Physiol.*, 256(2 Pt 2):R443-R447, Feb. 1989.

(56) References Cited

OTHER PUBLICATIONS

Deng, "Targeted drug delivery across the blood-brain barrier using ultrasound technique," *Ther Deliv.*, 1(6):819-848, Dec. 2010.
Egleton and Davis, "Bioavailability and transport of peptides and peptide drugs into the brain," *Peptides*, 18(9):1431-1439, 1997.
Goldstein and Betz, "The blood-brain barrier," *Sci Am.*, 255(3):74-83, Sep. 1986.
Greig et al., "Pharmacokinetics of chlorambucil-tertiary butyl ester, a lipophilic chlorambucil derivative that achieves and maintains high concentrations in brain," *Cancer Chemother Pharmacol.*, 25(5):320-325, 1990.
Hdeib and Sloan, "Convection-enhanced delivery of 131I-chTNT-1/B mAB for treatment of high-grade adult gliomas," *Expert Opin Biol Ther.*, 11(6):799-806. Epub Apr. 27, 2011.
Hervé et al., "CNS delivery via adsorptive transcytosis," *AAPS J.*, 10(3):455-472, Epub Aug. 26, 2008.
Hoey and Smith, "Chemistry of Constrast Media," *Radiocontrast Agents*, Sovak, ed. vol. 73 pp. 23-125 (1984).
Hynynen et al., "Focal disruption of the blood-brain barrier due to 260-kHz ultrasound bursts: a method for molecular imaging and targeted drug delivery," *J Neurosurg.*, 105(3):445-454, Sep. 2006.
Kioi et al., "Convection-enhanced delivery of interleukin-13 receptor-directed cytotoxin for malignant glioma therapy," *Technol Cancer Res Treat.*, 5(3):239-250, Jun. 2006.
Marquet et al., "Noninvasive, transient and selective blood-brain barrier opening in non-human primates in vivo," *PLoS One.*, 6(7):e22598, Epub Jul. 22, 2011.
Martín et al., "Design, synthesis and characterization of a new anionic cell-penetrating peptide: SAP(E)," *Chembiochem.*, 12(6):896-903, Epub Mar. 1, 2011.
Mesiwala et al., "High-intensity focused ultrasound selectively disrupts the blood-brain barrier in vivo," *Ultrasound Med Biol.*, 28(3):389-400, Mar. 2002.
Rayudu, *Radiotracers for Medical Applications*, vol. 1, pp. 201, Apr. 6, 1983.
Reese and Karnovsky, "Fine structural localization of a blood-brain barrier to exogenous peroxidase," *J Cell Biol.*, 34(1):207-217, Jul. 1967.
Scheld, "Drug delivery to the central nervous system: general principles and relevance to therapy for infections infections of the central nervous system," *Rev Infect Dis.*, 11 Suppl 7:S1669-S1690, Nov.-Dec. 1989.
Sheikov et al., "Cellular mechanisms of the blood-brain barrier opening induced by ultrasound in presence of microbubbles," *Ultrasound Med Biol.*, 30(7):979-989, Jul. 2004.
Tyler et al., "In vivo enhancement of ultrasonic image luminance by aqueous solutions with high speed of sound," *Ultrasonic Imaging*, 3, pp. 323-329, 1981.
van de Waterbeemd, "Estimation of blood-brain barrier crossing of drugs using molecular size and shape, and H-bonding descriptors," *J Drug Target.*, 6(2):151-165, 1998.
Waterhouse, "Determination of lipophilicity and its use as a predictor of blood-brain barrier penetration of molecular imaging agents," *Mol Imaging Biol.*, 5(6):376-389, Nov.-Dec. 2003.
European Search Report for Application No. 10800456, dated Dec. 21, 2012, 5 pages.

\* cited by examiner

SEQUENCE LISTING

```
<160> NUMBER OF SEQ ID NOS: 143

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Lys Lys Lys
1

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Lys Lys Lys Lys Lys Lys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Lys Lys Lys Lys Lys Lys Lys Lys Lys Lys
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Lys Lys Lys Lys Lys Lys Lys Lys Lys Lys Lys Lys Lys Lys Lys
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg
1
```

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Arg Arg Arg Arg
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Arg Arg Arg Arg Arg Arg
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Arg Arg Arg Arg Arg Arg Arg Arg Arg Arg Arg Arg Arg Arg
1               5                   10                  15

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Arg Lys Arg
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Lys Lys Arg
1

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 11

Lys Lys Lys Arg Arg Arg Lys Lys Lys Arg Arg Arg
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Lys Lys Arg Arg Arg Arg Lys Lys Lys Lys Arg Arg Arg Arg
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg Val Arg Leu Ala Ser His Leu Arg Lys Leu Arg Lys Arg Leu
1               5                   10                  15

Leu Arg Asp Ala
            20

<210> SEQ ID NO 14
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Ser Val Ile Asp Ala Leu Gln Tyr Lys Leu Glu Gly Thr Thr Arg
1               5                   10                  15

Leu Thr Arg Lys Arg Gly Leu Lys Leu Ala Thr Ala Leu Ser Leu Ser
            20                  25                  30

Asn Lys Phe Val Glu Gly Ser His
        35                  40

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Tyr or a Tyr derivative

<400> SEQUENCE: 15

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Xaa
```

```
<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Tyr or a Tyr derivative

<400> SEQUENCE: 16

Ala Lys Pro Glu Ala Pro Gly Glu Asp Ala Ser Pro Glu Glu Leu Ser
1               5                   10                  15

Arg Tyr Tyr Ala Ser Leu Arg His Tyr Leu Asn Leu Val Thr Arg Gln
            20                  25                  30

Arg Xaa

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Tyr or a Tyr derivative

<400> SEQUENCE: 17

Tyr Pro Ser Asp Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Xaa
            35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Tyr or a Tyr derivative

<400> SEQUENCE: 18

Ala Pro Leu Glu Pro Val Tyr Pro Gly Asp Asp Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Xaa
            35

<210> SEQ ID NO 19
<211> LENGTH: 24
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 19

Lys Lys Lys Lys Leu Arg Val Arg Leu Ala Ser His Leu Arg Lys Leu
1               5                   10                  15

Arg Lys Arg Leu Leu Arg Asp Ala
            20

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 20

Lys Lys Lys Lys Lys Lys Lys Lys Leu Arg Val Arg Leu Ala Ser His
1               5                   10                  15

Leu Arg Lys Leu Arg Lys Arg Leu Leu Arg Asp Ala
            20                  25

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 21

Lys Lys Lys Lys Lys Lys Lys Lys Lys Lys Lys Lys Leu Arg Val Arg
1               5                   10                  15

Leu Ala Ser His Leu Arg Lys Leu Arg Lys Arg Leu Leu Arg Asp Ala
            20                  25                  30

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 22

Lys Lys Lys Lys Lys Lys Lys Lys Lys Lys Lys Lys Lys Lys Lys Lys
1               5                   10                  15

Leu Arg Val Arg Leu Ala Ser His Leu Arg Lys Leu Arg Lys Arg Leu
            20                  25                  30

Leu Arg Asp Ala
        35

<210> SEQ ID NO 23
<211> LENGTH: 40
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

Lys Lys Lys Lys Lys Lys Lys Lys Lys Lys Lys Lys Lys Lys Lys Lys
1               5                   10                  15

-continued

```
Lys Lys Lys Lys Leu Arg Val Arg Leu Ala Ser His Leu Arg Lys Leu
            20                  25                  30

Arg Lys Arg Leu Leu Arg Asp Ala
        35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Lys Lys Lys Lys Ser Ser Val Ile Asp Ala Leu Gln Tyr Lys Leu Glu
1               5                   10                  15

Gly Thr Thr Arg Leu Thr Arg Lys Arg Gly Leu Lys Leu Ala Thr Ala
            20                  25                  30

Leu Ser Leu Ser Asn Lys Phe Val Glu Gly Ser His
        35                  40

<210> SEQ ID NO 25
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Lys Lys Lys Lys Lys Lys Lys Ser Ser Val Ile Asp Ala Leu Gln
1               5                   10                  15

Tyr Lys Leu Glu Gly Thr Thr Arg Leu Thr Arg Lys Arg Gly Leu Lys
            20                  25                  30

Leu Ala Thr Ala Leu Ser Leu Ser Asn Lys Phe Val Glu Gly Ser His
        35                  40                  45

<210> SEQ ID NO 26
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Lys Lys Lys Lys Lys Lys Lys Lys Lys Ser Ser Val Ile
1               5                   10                  15

Asp Ala Leu Gln Tyr Lys Leu Glu Gly Thr Thr Arg Leu Thr Arg Lys
            20                  25                  30

Arg Gly Leu Lys Leu Ala Thr Ala Leu Ser Leu Ser Asn Lys Phe Val
        35                  40                  45

Glu Gly Ser His
    50

<210> SEQ ID NO 27
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Lys Lys Lys Lys Lys Lys Lys Lys Lys Lys Lys Lys Lys Lys Lys
1               5                   10                  15

Ser Ser Val Ile Asp Ala Leu Gln Tyr Lys Leu Glu Gly Thr Thr Arg
            20                  25                  30

Leu Thr Arg Lys Arg Gly Leu Lys Leu Ala Thr Ala Leu Ser Leu Ser
        35                  40                  45

Asn Lys Phe Val Glu Gly Ser His
        50                  55

<210> SEQ ID NO 28
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Lys Lys Lys Lys Lys Lys Lys Lys Lys Lys Lys Lys Lys Lys
1               5                   10                  15

Lys Lys Lys Lys Ser Ser Val Ile Asp Ala Leu Gln Tyr Lys Leu Glu
            20                  25                  30

Gly Thr Thr Arg Leu Thr Arg Lys Arg Gly Leu Lys Leu Ala Thr Ala
        35                  40                  45

Leu Ser Leu Ser Asn Lys Phe Val Glu Gly Ser His
        50                  55                  60

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Leu, Ser, or Val
<220> FEATURE:
<221> NAME/KEY: MOD_RES
<222> LOCATION: (5)..(5)
<223> OTHER INFORMATION: Leu or Met
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
<222> LOCATION: (7)..(7)
<223> OTHER INFORMATION: Asn, Ser, or Thr
<220> FEATURE:
<221> NAME/KEY: MOD_RES
<222> LOCATION: (11)..(11)
<223> OTHER INFORMATION: Lys or Asn
<220> FEATURE:
<221> NAME/KEY: MOD_RES
<222> LOCATION: (12)..(12)
<223> OTHER INFORMATION: Leu, Met, or Val
<220> FEATURE:
<221> NAME/KEY: MOD_RES
<222> LOCATION: (13)..(13)
<223> OTHER INFORMATION: Arg or Pro
<220> FEATURE:
<221> NAME/KEY: MOD_RES
<222> LOCATION: (17)..(17)
<223> OTHER INFORMATION: Leu or Met
<220> FEATURE:
<221> NAME/KEY: MOD_RES
<222> LOCATION: (20)..(20)
```

<223> OTHER INFORMATION: Ala or Leu

<400> SEQUENCE: 29

Leu Arg Xaa Arg Xaa Xaa Xaa His Leu Arg Xaa Xaa Xaa Lys Arg Leu
1               5                   10                  15

Xaa Arg Asp Xaa
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Arg Ser Arg Leu Ala Ser His Leu Arg Lys Leu Arg Lys Arg Leu
1               5                   10                  15

Leu Arg Asp Ala
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Arg Val Arg Met Ala Ser His Leu Arg Lys Leu Arg Lys Arg Leu
1               5                   10                  15

Leu Arg Asp Ala
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Arg Val Arg Leu Ala Thr His Leu Arg Lys Leu Arg Lys Arg Leu
1               5                   10                  15

Leu Arg Asp Ala
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Val Arg Leu Ala Ser His Leu Arg Lys Leu Pro Lys Arg Leu
1               5                   10                  15

Leu Arg Asp Ala
            20

```
<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Arg Val Arg Leu Ala Ser His Leu Arg Lys Leu Arg Lys Arg Leu
1               5                  10                  15

Met Arg Asp Ala
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Val Arg Leu Ala Ser His Leu Arg Asn Leu Arg Lys Arg Leu
1               5                  10                  15

Leu Arg Asp Ala
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Arg Val Arg Leu Ala Ser His Leu Arg Lys Val Arg Lys Arg Leu
1               5                  10                  15

Leu Arg Asp Ala
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Arg Val Arg Met Ser Ser His Leu Arg Lys Leu Arg Lys Arg Leu
1               5                  10                  15

Leu Arg Asp Ala
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Arg Val Arg Leu Ala Ser His Leu Arg Asn Val Arg Lys Arg Leu
```

```
1               5                  10                 15

Leu Arg Asp Ala
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Arg Val Arg Leu Ala Ser His Leu Arg Asn Met Arg Lys Arg Leu
1               5                  10                 15

Leu Arg Asp Ala
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Arg Ala Arg Met Ala Ser His Leu Arg Lys Leu Arg Lys Arg Leu
1               5                  10                 15

Leu Arg Asp Ala
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Arg Val Arg Leu Ser Ser His Leu Arg Lys Leu Arg Lys Arg Leu
1               5                  10                 15

Met Arg Asp Ala
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Arg Ser Arg Leu Ala Ser His Leu Arg Lys Leu Arg Lys Arg Leu
1               5                  10                 15

Met Arg Asp Ala
            20

<210> SEQ ID NO 43
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 43

Leu Arg Val Arg Leu Ser Ser His Leu Pro Lys Leu Arg Lys Arg Leu
1               5                   10                  15

Leu Arg Asp Ala
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Arg Val Arg Leu Ala Ser His Leu Arg Lys Met Arg Lys Arg Leu
1               5                   10                  15

Met Arg Asp Ala
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Arg Val Arg Leu Ala Ser His Leu Arg Asn Leu Pro Lys Arg Leu
1               5                   10                  15

Leu Arg Asp Ala
            20

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Lys Lys Lys Leu Arg Ser Arg Leu Ala Ser His Leu Arg Lys Leu
1               5                   10                  15

Arg Lys Arg Leu Leu Arg Asp Ala
            20

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Lys Lys Lys Lys Lys Lys Lys Leu Arg Ser Arg Leu Ala Ser His
1               5                   10                  15

Leu Arg Lys Leu Arg Lys Arg Leu Leu Arg Asp Ala
            20                  25
```

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Lys Lys Lys Lys Lys Lys Lys Lys Lys Lys Lys Lys Leu Arg Ser Arg
1               5                   10                  15

Leu Ala Ser His Leu Arg Lys Leu Arg Lys Arg Leu Leu Arg Asp Ala
            20                  25                  30

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Lys Lys Lys Lys Lys Lys Lys Lys Lys Lys Lys Lys Lys Lys Lys Lys
1               5                   10                  15

Leu Arg Ser Arg Leu Ala Ser His Leu Arg Lys Leu Arg Lys Arg Leu
            20                  25                  30

Leu Arg Asp Ala
        35

<210> SEQ ID NO 50
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Lys Lys Lys Lys Lys Lys Lys Lys Lys Lys Lys Lys Lys Lys Lys Lys
1               5                   10                  15

Lys Lys Lys Lys Leu Arg Ser Arg Leu Ala Ser His Leu Arg Lys Leu
            20                  25                  30

Arg Lys Arg Leu Leu Arg Asp Ala
        35                  40

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Lys Lys Lys Leu Arg Val Arg Met Ala Ser His Leu Arg Lys Leu
1               5                   10                  15

Arg Lys Arg Leu Leu Arg Asp Ala
            20

<210> SEQ ID NO 52
<211> LENGTH: 28
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 52

Lys Lys Lys Lys Lys Lys Lys Lys Leu Arg Val Arg Met Ala Ser His
1               5                   10                  15

Leu Arg Lys Leu Arg Lys Arg Leu Leu Arg Asp Ala
            20                  25

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Lys Lys Lys Lys Lys Lys Lys Lys Lys Lys Lys Lys Leu Arg Val Arg
1               5                   10                  15

Met Ala Ser His Leu Arg Lys Leu Arg Lys Arg Leu Leu Arg Asp Ala
            20                  25                  30

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Lys Lys Lys Lys Lys Lys Lys Lys Lys Lys Lys Lys Lys Lys Lys Lys
1               5                   10                  15

Leu Arg Val Arg Met Ala Ser His Leu Arg Lys Leu Arg Lys Arg Leu
            20                  25                  30

Leu Arg Asp Ala
        35

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Lys Lys Lys Lys Lys Lys Lys Lys Lys Lys Lys Lys Lys Lys Lys
1               5                   10                  15

Lys Lys Lys Lys Leu Arg Val Arg Met Ala Ser His Leu Arg Lys Leu
            20                  25                  30

Arg Lys Arg Leu Leu Arg Asp Ala
        35                  40

<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56
```

Lys Lys Lys Lys Leu Arg Val Arg Leu Ala Thr His Leu Arg Lys Leu
1               5                   10                  15

Arg Lys Arg Leu Leu Arg Asp Ala
            20

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Lys Lys Lys Lys Lys Lys Lys Leu Arg Val Arg Leu Ala Thr His
1               5                   10                  15

Leu Arg Lys Leu Arg Lys Arg Leu Leu Arg Asp Ala
            20                  25

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Lys Lys Lys Lys Lys Lys Lys Lys Lys Lys Lys Lys Leu Arg Val Arg
1               5                   10                  15

Leu Ala Thr His Leu Arg Lys Leu Arg Lys Arg Leu Leu Arg Asp Ala
            20                  25                  30

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Lys Lys Lys Lys Lys Lys Lys Lys Lys Lys Lys Lys Lys Lys Lys Lys
1               5                   10                  15

Leu Arg Val Arg Leu Ala Thr His Leu Arg Lys Leu Arg Lys Arg Leu
            20                  25                  30

Leu Arg Asp Ala
            35

<210> SEQ ID NO 60
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Lys Lys Lys Lys Lys Lys Lys Lys Lys Lys Lys Lys Lys Lys Lys Lys
1               5                   10                  15

Lys Lys Lys Lys Leu Arg Val Arg Leu Ala Thr His Leu Arg Lys Leu
            20                  25                  30

Arg Lys Arg Leu Leu Arg Asp Ala

```
                35                  40
```

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Lys Lys Lys Lys Leu Arg Val Arg Leu Ala Ser His Leu Arg Lys Leu
1               5                   10                  15

Pro Lys Arg Leu Leu Arg Asp Ala
            20
```

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Lys Lys Lys Lys Lys Lys Lys Lys Leu Arg Val Arg Leu Ala Ser His
1               5                   10                  15

Leu Arg Lys Leu Pro Lys Arg Leu Leu Arg Asp Ala
            20                  25
```

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Lys Lys Lys Lys Lys Lys Lys Lys Lys Lys Lys Lys Leu Arg Val Arg
1               5                   10                  15

Leu Ala Ser His Leu Arg Lys Leu Pro Lys Arg Leu Leu Arg Asp Ala
            20                  25                  30
```

<210> SEQ ID NO 64
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Lys Lys Lys Lys Lys Lys Lys Lys Lys Lys Lys Lys Lys Lys Lys Lys
1               5                   10                  15

Leu Arg Val Arg Leu Ala Ser His Leu Arg Lys Leu Pro Lys Arg Leu
            20                  25                  30

Leu Arg Asp Ala
        35
```

<210> SEQ ID NO 65
<211> LENGTH: 40
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 65

Lys Lys Lys Lys Lys Lys Lys Lys Lys Lys Lys Lys Lys Lys Lys
1               5                   10                  15

Lys Lys Lys Lys Leu Arg Val Arg Leu Ala Ser His Leu Arg Lys Leu
                20                  25                  30

Pro Lys Arg Leu Leu Arg Asp Ala
        35                  40

<210> SEQ ID NO 66
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Lys Lys Lys Leu Arg Val Arg Leu Ala Ser His Leu Arg Lys Leu
1               5                   10                  15

Arg Lys Arg Leu Met Arg Asp Ala
                20

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Lys Lys Lys Lys Lys Lys Lys Leu Arg Val Arg Leu Ala Ser His
1               5                   10                  15

Leu Arg Lys Leu Arg Lys Arg Leu Met Arg Asp Ala
                20                  25

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Lys Lys Lys Lys Lys Lys Lys Lys Lys Lys Lys Lys Leu Arg Val Arg
1               5                   10                  15

Leu Ala Ser His Leu Arg Lys Leu Arg Lys Arg Leu Met Arg Asp Ala
                20                  25                  30

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Lys Lys Lys Lys Lys Lys Lys Lys Lys Lys Lys Lys Lys Lys Lys
1               5                   10                  15
```

```
Leu Arg Val Arg Leu Ala Ser His Leu Arg Lys Leu Arg Lys Arg Leu
            20                  25                  30

Met Arg Asp Ala
        35
```

<210> SEQ ID NO 70
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Lys Lys Lys Lys Lys Lys Lys Lys Lys Lys Lys Lys Lys Lys Lys Lys
1               5                   10                  15

Lys Lys Lys Lys Leu Arg Val Arg Leu Ala Ser His Leu Arg Lys Leu
            20                  25                  30

Arg Lys Arg Leu Met Arg Asp Ala
        35                  40
```

<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Lys Lys Lys Lys Leu Arg Val Arg Leu Ala Ser His Leu Arg Asn Leu
1               5                   10                  15

Arg Lys Arg Leu Leu Arg Asp Ala
            20
```

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Lys Lys Lys Lys Lys Lys Lys Lys Leu Arg Val Arg Leu Ala Ser His
1               5                   10                  15

Leu Arg Asn Leu Arg Lys Arg Leu Leu Arg Asp Ala
            20                  25
```

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Lys Lys Lys Lys Lys Lys Lys Lys Lys Lys Lys Lys Leu Arg Val Arg
1               5                   10                  15

Leu Ala Ser His Leu Arg Asn Leu Arg Lys Arg Leu Leu Arg Asp Ala
            20                  25                  30
```

<210> SEQ ID NO 74

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Lys Lys Lys Lys Lys Lys Lys Lys Lys Lys Lys Lys Lys Lys Lys Lys
1               5                   10                  15

Leu Arg Val Arg Leu Ala Ser His Leu Arg Asn Leu Arg Lys Arg Leu
            20                  25                  30

Leu Arg Asp Ala
        35

<210> SEQ ID NO 75
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Lys Lys Lys Lys Lys Lys Lys Lys Lys Lys Lys Lys Lys Lys Lys Lys
1               5                   10                  15

Lys Lys Lys Lys Leu Arg Val Arg Leu Ala Ser His Leu Arg Asn Leu
            20                  25                  30

Arg Lys Arg Leu Leu Arg Asp Ala
        35                  40

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Lys Lys Lys Leu Arg Val Arg Leu Ala Ser His Leu Arg Lys Val
1               5                   10                  15

Arg Lys Arg Leu Leu Arg Asp Ala
            20

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Lys Lys Lys Lys Lys Lys Lys Leu Arg Val Arg Leu Ala Ser His
1               5                   10                  15

Leu Arg Lys Val Arg Lys Arg Leu Leu Arg Asp Ala
            20                  25

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
```

```
                              polypeptide

<400> SEQUENCE: 78

Lys Lys Lys Lys Lys Lys Lys Lys Lys Lys Lys Leu Arg Val Arg
1               5                   10                  15

Leu Ala Ser His Leu Arg Lys Val Arg Lys Arg Leu Leu Arg Asp Ala
            20                  25                  30

<210> SEQ ID NO 79
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Lys Lys Lys Lys Lys Lys Lys Lys Lys Lys Lys Lys Lys Lys Lys
1               5                   10                  15

Leu Arg Val Arg Leu Ala Ser His Leu Arg Lys Val Arg Lys Arg Leu
            20                  25                  30

Leu Arg Asp Ala
        35

<210> SEQ ID NO 80
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Lys Lys Lys Lys Lys Lys Lys Lys Lys Lys Lys Lys Lys Lys Lys
1               5                   10                  15

Lys Lys Lys Lys Leu Arg Val Arg Leu Ala Ser His Leu Arg Lys Val
            20                  25                  30

Arg Lys Arg Leu Leu Arg Asp Ala
        35                  40

<210> SEQ ID NO 81
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Lys Lys Lys Leu Arg Val Arg Met Ser Ser His Leu Arg Lys Leu
1               5                   10                  15

Arg Lys Arg Leu Leu Arg Asp Ala
            20

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Lys Lys Lys Lys Lys Lys Lys Leu Arg Val Arg Met Ser Ser His
```

```
                    1               5                  10                  15
Leu Arg Lys Leu Arg Lys Arg Leu Leu Arg Asp Ala
            20                  25

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Lys Lys Lys Lys Lys Lys Lys Lys Lys Lys Lys Leu Arg Val Arg
1               5                  10                  15

Met Ser Ser His Leu Arg Lys Leu Arg Lys Arg Leu Leu Arg Asp Ala
            20                  25                  30

<210> SEQ ID NO 84
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Lys Lys Lys Lys Lys Lys Lys Lys Lys Lys Lys Lys Lys Lys Lys
1               5                  10                  15

Leu Arg Val Arg Met Ser Ser His Leu Arg Lys Leu Arg Lys Arg Leu
            20                  25                  30

Leu Arg Asp Ala
        35

<210> SEQ ID NO 85
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Lys Lys Lys Lys Lys Lys Lys Lys Lys Lys Lys Lys Lys Lys Lys
1               5                  10                  15

Lys Lys Lys Lys Leu Arg Val Arg Met Ser Ser His Leu Arg Lys Leu
            20                  25                  30

Arg Lys Arg Leu Leu Arg Asp Ala
        35                  40

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Lys Lys Lys Leu Arg Val Arg Leu Ala Ser His Leu Arg Asn Val
1               5                  10                  15

Arg Lys Arg Leu Leu Arg Asp Ala
            20
```

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys Lys Lys Lys Lys Lys Lys Lys Leu Arg Val Arg Leu Ala Ser His
1               5                   10                  15

Leu Arg Asn Val Arg Lys Arg Leu Leu Arg Asp Ala
            20                  25

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Lys Lys Lys Lys Lys Lys Lys Lys Lys Lys Lys Leu Arg Val Arg
1               5                   10                  15

Leu Ala Ser His Leu Arg Asn Val Arg Lys Arg Leu Leu Arg Asp Ala
            20                  25                  30

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Lys Lys Lys Lys Lys Lys Lys Lys Lys Lys Lys Lys Lys Lys Lys Lys
1               5                   10                  15

Leu Arg Val Arg Leu Ala Ser His Leu Arg Asn Val Arg Lys Arg Leu
            20                  25                  30

Leu Arg Asp Ala
        35

<210> SEQ ID NO 90
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Lys Lys Lys Lys Lys Lys Lys Lys Lys Lys Lys Lys Lys Lys Lys Lys
1               5                   10                  15

Lys Lys Lys Lys Leu Arg Val Arg Leu Ala Ser His Leu Arg Asn Val
            20                  25                  30

Arg Lys Arg Leu Leu Arg Asp Ala
        35                  40

<210> SEQ ID NO 91
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 91

Lys Lys Lys Lys Leu Arg Val Arg Leu Ala Ser His Leu Arg Asn Met
1               5                   10                  15

Arg Lys Arg Leu Leu Arg Asp Ala
            20

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Lys Lys Lys Lys Lys Lys Lys Leu Arg Val Arg Leu Ala Ser His
1               5                   10                  15

Leu Arg Asn Met Arg Lys Arg Leu Leu Arg Asp Ala
            20                  25

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Lys Lys Lys Lys Lys Lys Lys Lys Lys Lys Lys Lys Leu Arg Val Arg
1               5                   10                  15

Leu Ala Ser His Leu Arg Asn Met Arg Lys Arg Leu Leu Arg Asp Ala
            20                  25                  30

<210> SEQ ID NO 94
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Lys Lys Lys Lys Lys Lys Lys Lys Lys Lys Lys Lys Lys Lys Lys Lys
1               5                   10                  15

Leu Arg Val Arg Leu Ala Ser His Leu Arg Asn Met Arg Lys Arg Leu
            20                  25                  30

Leu Arg Asp Ala
        35

<210> SEQ ID NO 95
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Lys Lys Lys Lys Lys Lys Lys Lys Lys Lys Lys Lys Lys Lys Lys Lys
1               5                   10                  15
```

```
Lys Lys Lys Lys Leu Arg Val Arg Leu Ala Ser His Leu Arg Asn Met
                20                  25                  30

Arg Lys Arg Leu Leu Arg Asp Ala
            35                  40

<210> SEQ ID NO 96
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Lys Lys Lys Leu Arg Ala Arg Met Ala Ser His Leu Arg Lys Leu
1               5                   10                  15

Arg Lys Arg Leu Leu Arg Asp Ala
            20

<210> SEQ ID NO 97
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Lys Lys Lys Lys Lys Lys Lys Leu Arg Ala Arg Met Ala Ser His
1               5                   10                  15

Leu Arg Lys Leu Arg Lys Arg Leu Leu Arg Asp Ala
            20                  25

<210> SEQ ID NO 98
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Lys Lys Lys Lys Lys Lys Lys Lys Lys Lys Lys Lys Leu Arg Ala Arg
1               5                   10                  15

Met Ala Ser His Leu Arg Lys Leu Arg Lys Arg Leu Leu Arg Asp Ala
            20                  25                  30

<210> SEQ ID NO 99
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Lys Lys Lys Lys Lys Lys Lys Lys Lys Lys Lys Lys Lys Lys Lys Lys
1               5                   10                  15

Leu Arg Ala Arg Met Ala Ser His Leu Arg Lys Leu Arg Lys Arg Leu
            20                  25                  30

Leu Arg Asp Ala
        35
```

```
<210> SEQ ID NO 100
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Lys Lys Lys Lys Lys Lys Lys Lys Lys Lys Lys Lys Lys Lys Lys Lys
1               5                   10                  15

Lys Lys Lys Lys Leu Arg Ala Arg Met Ala Ser His Leu Arg Lys Leu
                20                  25                  30

Arg Lys Arg Leu Leu Arg Asp Ala
            35                  40

<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Lys Lys Lys Leu Arg Val Arg Leu Ser Ser His Leu Arg Lys Leu
1               5                   10                  15

Arg Lys Arg Leu Met Arg Asp Ala
            20

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Lys Lys Lys Lys Lys Lys Lys Leu Arg Val Arg Leu Ser Ser His
1               5                   10                  15

Leu Arg Lys Leu Arg Lys Arg Leu Met Arg Asp Ala
            20                  25

<210> SEQ ID NO 103
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Lys Lys Lys Lys Lys Lys Lys Lys Lys Lys Lys Lys Leu Arg Val Arg
1               5                   10                  15

Leu Ser Ser His Leu Arg Lys Leu Arg Lys Arg Leu Met Arg Asp Ala
            20                  25                  30

<210> SEQ ID NO 104
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 104

Lys Lys Lys Lys Lys Lys Lys Lys Lys Lys Lys Lys Lys Lys Lys
1               5                   10                  15

Leu Arg Val Arg Leu Ser Ser His Leu Arg Lys Leu Arg Lys Arg Leu
            20                  25                  30

Met Arg Asp Ala
        35

<210> SEQ ID NO 105
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Lys Lys Lys Lys Lys Lys Lys Lys Lys Lys Lys Lys Lys Lys Lys
1               5                   10                  15

Lys Lys Lys Lys Leu Arg Val Arg Leu Ser Ser His Leu Arg Lys Leu
            20                  25                  30

Arg Lys Arg Leu Met Arg Asp Ala
        35                  40

<210> SEQ ID NO 106
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Lys Lys Lys Leu Arg Ser Arg Leu Ala Ser His Leu Arg Lys Leu
1               5                   10                  15

Arg Lys Arg Leu Met Arg Asp Ala
            20

<210> SEQ ID NO 107
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Lys Lys Lys Lys Lys Lys Lys Leu Arg Ser Arg Leu Ala Ser His
1               5                   10                  15

Leu Arg Lys Leu Arg Lys Arg Leu Met Arg Asp Ala
            20                  25

<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Lys Lys Lys Lys Lys Lys Lys Lys Lys Lys Lys Lys Leu Arg Ser Arg
1               5                   10                  15

Leu Ala Ser His Leu Arg Lys Leu Arg Lys Arg Leu Met Arg Asp Ala
                20                  25                  30

<210> SEQ ID NO 109
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Lys Lys Lys Lys Lys Lys Lys Lys Lys Lys Lys Lys Lys Lys Lys Lys
1               5                   10                  15

Leu Arg Ser Arg Leu Ala Ser His Leu Arg Lys Leu Arg Lys Arg Leu
                20                  25                  30

Met Arg Asp Ala
        35

<210> SEQ ID NO 110
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Lys Lys Lys Lys Lys Lys Lys Lys Lys Lys Lys Lys Lys Lys Lys Lys
1               5                   10                  15

Lys Lys Lys Lys Leu Arg Ser Arg Leu Ala Ser His Leu Arg Lys Leu
                20                  25                  30

Arg Lys Arg Leu Met Arg Asp Ala
        35                  40

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Lys Lys Lys Leu Arg Val Arg Leu Ser Ser His Leu Pro Lys Leu
1               5                   10                  15

Arg Lys Arg Leu Leu Arg Asp Ala
                20

<210> SEQ ID NO 112
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Lys Lys Lys Lys Lys Lys Lys Leu Arg Val Arg Leu Ser Ser His
1               5                   10                  15

Leu Pro Lys Leu Arg Lys Arg Leu Leu Arg Asp Ala
                20                  25

<210> SEQ ID NO 113

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Lys Lys Lys Lys Lys Lys Lys Lys Lys Lys Lys Leu Arg Val Arg
1               5                   10                  15

Leu Ser Ser His Leu Pro Lys Leu Arg Lys Arg Leu Leu Arg Asp Ala
            20                  25                  30

<210> SEQ ID NO 114
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Lys Lys Lys Lys Lys Lys Lys Lys Lys Lys Lys Lys Lys Lys Lys
1               5                   10                  15

Leu Arg Val Arg Leu Ser Ser His Leu Pro Lys Leu Arg Lys Arg Leu
            20                  25                  30

Leu Arg Asp Ala
        35

<210> SEQ ID NO 115
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Lys Lys Lys Lys Lys Lys Lys Lys Lys Lys Lys Lys Lys Lys Lys
1               5                   10                  15

Lys Lys Lys Lys Leu Arg Val Arg Leu Ser Ser His Leu Pro Lys Leu
            20                  25                  30

Arg Lys Arg Leu Leu Arg Asp Ala
        35                  40

<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Lys Lys Lys Leu Arg Val Arg Leu Ala Ser His Leu Arg Lys Met
1               5                   10                  15

Arg Lys Arg Leu Met Arg Asp Ala
            20

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 117

Lys Lys Lys Lys Lys Lys Lys Leu Arg Val Arg Leu Ala Ser His
1               5                   10                  15

Leu Arg Lys Met Arg Lys Arg Leu Met Arg Asp Ala
            20                  25

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Lys Lys Lys Lys Lys Lys Lys Lys Lys Lys Leu Arg Val Arg
1               5                   10                  15

Leu Ala Ser His Leu Arg Lys Met Arg Lys Arg Leu Met Arg Asp Ala
            20                  25                  30

<210> SEQ ID NO 119
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Lys Lys Lys Lys Lys Lys Lys Lys Lys Lys Lys Lys Lys Lys Lys
1               5                   10                  15

Leu Arg Val Arg Leu Ala Ser His Leu Arg Lys Met Arg Lys Arg Leu
            20                  25                  30

Met Arg Asp Ala
        35

<210> SEQ ID NO 120
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Lys Lys Lys Lys Lys Lys Lys Lys Lys Lys Lys Lys Lys Lys Lys
1               5                   10                  15

Lys Lys Lys Lys Leu Arg Val Arg Leu Ala Ser His Leu Arg Lys Met
            20                  25                  30

Arg Lys Arg Leu Met Arg Asp Ala
        35                  40

<210> SEQ ID NO 121
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Lys Lys Lys Leu Arg Val Arg Leu Ala Ser His Leu Arg Asn Leu

-continued

```
                 1               5                  10                  15
Pro Lys Arg Leu Leu Arg Asp Ala
                20

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Lys Lys Lys Lys Lys Lys Lys Leu Arg Val Arg Leu Ala Ser His
1               5                  10                  15

Leu Arg Asn Leu Pro Lys Arg Leu Leu Arg Asp Ala
                20                  25

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Lys Lys Lys Lys Lys Lys Lys Lys Lys Lys Lys Leu Arg Val Arg
1               5                  10                  15

Leu Ala Ser His Leu Arg Asn Leu Pro Lys Arg Leu Leu Arg Asp Ala
                20                  25                  30

<210> SEQ ID NO 124
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Lys Lys Lys Lys Lys Lys Lys Lys Lys Lys Lys Lys Lys Lys Lys Lys
1               5                  10                  15

Leu Arg Val Arg Leu Ala Ser His Leu Arg Asn Leu Pro Lys Arg Leu
                20                  25                  30

Leu Arg Asp Ala
        35

<210> SEQ ID NO 125
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Lys Lys Lys Lys Lys Lys Lys Lys Lys Lys Lys Lys Lys Lys Lys Lys
1               5                  10                  15

Lys Lys Lys Lys Leu Arg Val Arg Leu Ala Ser His Leu Arg Asn Leu
                20                  25                  30

Pro Lys Arg Leu Leu Arg Asp Ala
        35                  40
```

```
<210> SEQ ID NO 126
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Lys Lys Lys Lys Lys Lys Lys Lys Lys Lys Lys Lys Lys Lys Lys Lys
1               5                   10                  15

Leu Arg Leu Arg Leu Ala Asn His Leu Arg Lys Leu Arg Lys Arg Leu
            20                  25                  30

Leu Arg Asp Ala
        35

<210> SEQ ID NO 127
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Lys Lys Lys Lys Lys Lys Lys Lys Lys Lys Lys Lys Lys Lys Lys Lys
1               5                   10                  15

Leu Arg Leu Arg Leu Ala Ser His Leu Arg Lys Leu Arg Lys Arg Leu
            20                  25                  30

Leu Arg Asp Leu
        35

<210> SEQ ID NO 128
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Lys Lys Lys Lys Lys Lys Lys Lys Lys Lys Lys Lys Lys Lys Lys Lys
1               5                   10                  15

Leu Arg Val Arg Leu Ala Asn His Leu Arg Lys Leu Arg Lys Arg Leu
            20                  25                  30

Leu Arg Asp Leu
        35

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Arg Leu Arg Leu Ala Ser His Leu Arg Lys Leu Arg Lys Arg Leu
1               5                   10                  15

Leu Arg Asp Leu
            20

<210> SEQ ID NO 130
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Leu Arg Val Arg Leu Ala Asn His Leu Arg Lys Leu Arg Lys Arg Leu
1               5                   10                  15

Leu Arg Asp Leu
            20

<210> SEQ ID NO 131
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Lys Lys Lys Leu Arg Leu Arg Leu Ala Ser His Leu Arg Lys Leu
1               5                   10                  15

Arg Lys Arg Leu Leu Arg Asp Leu
            20

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Lys Lys Lys Lys Lys Lys Lys Leu Arg Leu Arg Leu Ala Ser His
1               5                   10                  15

Leu Arg Lys Leu Arg Lys Arg Leu Leu Arg Asp Leu
            20                  25

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Lys Lys Lys Lys Lys Lys Lys Lys Lys Lys Lys Lys Leu Arg Leu Arg
1               5                   10                  15

Leu Ala Ser His Leu Arg Lys Leu Arg Lys Arg Leu Leu Arg Asp Leu
            20                  25                  30

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Lys Lys Lys Lys Lys Lys Lys Lys Lys Lys Lys Lys Lys Lys Lys Lys
1               5                   10                  15
```

Leu Arg Leu Arg Leu Ala Ser His Leu Arg Lys Leu Arg Lys Arg Leu
            20                  25                  30

Leu Arg Asp Leu
        35

<210> SEQ ID NO 135
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Lys Lys Lys Lys Lys Lys Lys Lys Lys Lys Lys Lys Lys Lys Lys Lys
1               5                   10                  15

Lys Lys Lys Lys Leu Arg Leu Arg Leu Ala Ser His Leu Arg Lys Leu
            20                  25                  30

Arg Lys Arg Leu Leu Arg Asp Leu
        35                  40

<210> SEQ ID NO 136
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Lys Lys Lys Leu Arg Val Arg Leu Ala Asn His Leu Arg Lys Leu
1               5                   10                  15

Arg Lys Arg Leu Leu Arg Asp Leu
            20

<210> SEQ ID NO 137
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Lys Lys Lys Lys Lys Lys Lys Leu Arg Val Arg Leu Ala Asn His
1               5                   10                  15

Leu Arg Lys Leu Arg Lys Arg Leu Leu Arg Asp Leu
            20                  25

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Lys Lys Lys Lys Lys Lys Lys Lys Lys Lys Lys Lys Leu Arg Val Arg
1               5                   10                  15

Leu Ala Asn His Leu Arg Lys Leu Arg Lys Arg Leu Leu Arg Asp Leu
            20                  25                  30

```
<210> SEQ ID NO 139
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Lys Lys Lys Lys Lys Lys Lys Lys Lys Lys Lys Lys Lys Lys Lys Lys
1               5                   10                  15

Leu Arg Val Arg Leu Ala Asn His Leu Arg Lys Leu Arg Lys Arg Leu
                20                  25                  30

Leu Arg Asp Leu
        35

<210> SEQ ID NO 140
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Lys Lys Lys Lys Lys Lys Lys Lys Lys Lys Lys Lys Lys Lys Lys Lys
1               5                   10                  15

Lys Lys Lys Lys Leu Arg Val Arg Leu Ala Asn His Leu Arg Lys Leu
                20                  25                  30

Arg Lys Arg Leu Leu Arg Asp Leu
        35                  40

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Arg Lys Leu Arg Lys Arg Leu Leu Arg Leu Lys Leu Arg Leu Lys
1               5                   10                  15

Arg Leu Leu Arg
        20

<210> SEQ ID NO 142
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: Hydrophilic amino acid and this region may
      encompass 4 to 20 residues
<220> FEATURE:
<221> NAME/KEY: MOD_RES
<222> LOCATION: (23)..(23)
<223> OTHER INFORMATION: Ala, Leu, Ser, or Val
<220> FEATURE:
<221> NAME/KEY: MOD_RES
<222> LOCATION: (25)..(25)
<223> OTHER INFORMATION: Leu or Met
<220> FEATURE:
<221> NAME/KEY: MOD_RES
```

```
<222> LOCATION: (26)..(26)
<223> OTHER INFORMATION: Ala or Ser
<220> FEATURE:
<221> NAME/KEY: MOD_RES
<222> LOCATION: (27)..(27)
<223> OTHER INFORMATION: Asn, Ser, or Thr
<220> FEATURE:
<221> NAME/KEY: MOD_RES
<222> LOCATION: (31)..(31)
<223> OTHER INFORMATION: Lys or Asn
<220> FEATURE:
<221> NAME/KEY: MOD_RES
<222> LOCATION: (32)..(32)
<223> OTHER INFORMATION: Leu, Met, or Val
<220> FEATURE:
<221> NAME/KEY: MOD_RES
<222> LOCATION: (33)..(33)
<223> OTHER INFORMATION: Arg or Pro
<220> FEATURE:
<221> NAME/KEY: MOD_RES
<222> LOCATION: (37)..(37)
<223> OTHER INFORMATION: Leu or Met
<220> FEATURE:
<221> NAME/KEY: MOD_RES
<222> LOCATION: (40)..(40)
<223> OTHER INFORMATION: Ala or Leu
<220> FEATURE:
<223> OTHER INFORMATION: see specification as filed for detailed
      description of substitutions and preferred embodiments

<400> SEQUENCE: 142

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Leu Arg Xaa Arg Xaa Xaa Xaa His Leu Arg Xaa Xaa
            20                  25                  30

Xaa Lys Arg Leu Xaa Arg Asp Xaa
        35                  40

<210> SEQ ID NO 143
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(50)
<223> OTHER INFORMATION: Hydrophilic amino acid and this region may
      encompass 4 to 50 residues
<220> FEATURE:
<221> NAME/KEY: MOD_RES
<222> LOCATION: (53)..(53)
<223> OTHER INFORMATION: Ala, Leu, Ser, or Val
<220> FEATURE:
<221> NAME/KEY: MOD_RES
<222> LOCATION: (55)..(55)
<223> OTHER INFORMATION: Leu or Met
<220> FEATURE:
<221> NAME/KEY: MOD_RES
<222> LOCATION: (56)..(56)
<223> OTHER INFORMATION: Ala or Ser
<220> FEATURE:
<221> NAME/KEY: MOD_RES
<222> LOCATION: (57)..(57)
<223> OTHER INFORMATION: Asn, Ser, or Thr
<220> FEATURE:
<221> NAME/KEY: MOD_RES
<222> LOCATION: (61)..(61)
<223> OTHER INFORMATION: Lys or Asn
<220> FEATURE:
<221> NAME/KEY: MOD_RES
<222> LOCATION: (62)..(62)
<223> OTHER INFORMATION: Leu, Met, or Val
<220> FEATURE:
```

```
<221> NAME/KEY: MOD_RES
<222> LOCATION: (63)..(63)
<223> OTHER INFORMATION: Arg or Pro
<220> FEATURE:
<221> NAME/KEY: MOD_RES
<222> LOCATION: (67)..(67)
<223> OTHER INFORMATION: Leu or Met
<220> FEATURE:
<221> NAME/KEY: MOD_RES
<222> LOCATION: (70)..(70)
<223> OTHER INFORMATION: Ala or Leu
<220> FEATURE:
<223> OTHER INFORMATION: see specification as filed for detailed
      description of substitutions and preferred embodiments

<400> SEQUENCE: 143

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Leu Arg Xaa Arg Xaa Xaa Xaa His Leu Arg Xaa Xaa Xaa Lys
    50                  55                  60

Arg Leu Xaa Arg Asp Xaa
65                  70
```

PEPTIDE-MEDIATED NON-COVALENT DELIVERY OF ACTIVE AGENTS ACROSS THE BLOOD-BRAIN BARRIER

CROSS-REFERENCE TO RELATED APPLICATIONS

This application is a divisional of U.S. application Ser. No. 13/383,710, filed Jan. 12, 2012, which is a National Stage application under 35 U.S.C. §371 of International Application No. PCT/US2010/041924, filed Jul. 14, 2010, which claims priority to U.S. Provisional Application Ser. No. 61/225,412, filed on Jul. 14, 2009, which is incorporated by reference in its entirety herein.

TECHNICAL FIELD

This disclosure relates to carrier peptides, including compositions and methods of using the same. In particular, the disclosure relates to carrier peptides capable of delivering active agents across the blood-brain barrier and compositions and methods of using the same.

BACKGROUND

The blood-brain barrier (BBB) prevents most macromolecules (e.g., DNA, RNA, and polypeptides) and many small molecules from entering the brain. The BBB is principally composed of specialized endothelial cells with highly restrictive tight junctions, consequently, passage of substances, small and large, from the blood into the central nervous system is controlled by the BBB. This structure makes treatment and management of patients with neurological diseases and disorders (e.g., brain cancer and Alzheimer's disease) difficult as many therapeutic agents cannot be delivered across the BBB with desirable efficiency.

SUMMARY

The peptides described herein can function as carrier peptides. These peptides can associate with (e.g., non-covalently bind) biologically active molecules and imaging agents to transport the biologically active molecules and imaging agents across the blood-brain barrier. In some cases, such transport may increase the effectiveness of the biological molecules and imaging agents.

A carrier peptide, as described herein, can include the sequence:

$X_n\text{-}[B]_m$ or a pharmaceutically acceptable salt thereof, wherein:
X is a hydrophilic amino acid;
B is a blood-brain barrier agent;
n is an integer from 4 to 50; and
m is integer from 1 to 3.

In some embodiments, the blood-brain barrier agent is not L-R-K-L-R-K-R-L-L-R-L-R-K-L-R-K-R-L-L-R (SEQ ID NO: 141).

A hydrophilic amino acid (X) can be chosen from arginine, asparagine, aspartic acid, glutamic acid, glutamine, histidine, lysine, serine, threonine, tyrosine, or a combination thereof. For example, in some embodiments, $X_n$ can comprise ten lysines and six arginines; six lysines and sixteen arginines; eight lysines, eight arginines, and eight histidines. In some embodiments, X is lysine.

The variable n is an integer ranging from 4 to 50 (e.g., 4, 6, 8, 10, 12, 16, 20, 24, 26, 28, 32, 36, 40, 42, 44, 48, and 50). In some embodiments, n is chosen from 4, 8, 12, 16, and 20. In some embodiments, n is 16. In some embodiments, m is 1.

The blood-brain barrier agent can be a receptor binding domain of an apolipoprotein. For example, the receptor binding domain of an apolipoprotein can be chosen from the receptor binding domain of ApoA, ApoB, ApoC, ApoD, ApoE, ApoE2, ApoE3, and ApoE4. In some embodiments, the receptor binding domain of an apolipoprotein is chosen from the receptor binding domain of ApoB and ApoE.

The blood-brain barrier agent can also include a polypeptide sequence having at least 80% sequence identity to:

(SEQ ID NO: 13)
L-R-V-R-L-A-S-H-L-R-K-L-R-K-R-L-L-R-D-A;

(SEQ ID NO: 14)
S-S-V-I-D-A-L-Q-Y-K-L-E-G-T-T-R-L-T-R-K-R-G-L-K-L-A-T-A-L-S-L-S-N-K-F-V-E-G-S-H;

(SEQ ID NO: 15)
Y-P-A-K-P-E-A-P-G-E-D-A-S-P-E-E-L-S-R-Y-Y-A-S-L-R-H-Y-L-N-L-V-T-R-Q-R-Y*;

(SEQ ID NO: 16)
A-K-P-E-A-P-G-E-D-A-S-P-E-E-L-S-R-Y-Y-A-S-L-R-H-Y-L-N-L-V-T-R-Q-R-Y*;

(SEQ ID NO: 17)
Y-P-S-D-P-D-N-P-G-E-D-A-P-A-E-D-L-A-R-Y-Y-S-A-L-R-H-Y-I-N-L-I-T-R-Q-R-Y*;
or (SEQ ID NO: 18)
A-P-L-E-P-V-Y-P-G-D-D-A-T-P-E-Q-M-A-Q-Y-A-A-E-L-R-R-Y-I-N-M-L-T-R-P-R-Y*, wherein Y* is tyrosine or a tyrosine derivative. In some embodiments, the polypeptide is less than 100 amino acids in length.

Examples of a carrier peptide can include:

(SEQ ID NO: 19)
K-K-K-L-R-V-R-L-A-S-H-L-R-K-L-R-K-R-L-L-R-D-A;

(SEQ ID NO: 20)
K-K-K-K-K-K-L-R-V-R-L-A-S-H-L-R-K-L-R-K-R-L-L-R-D-A;

(SEQ ID NO: 21)
K-K-K-K-K-K-K-K-K-L-R-V-R-L-A-S-H-L-R-K-L-R-K-R-L-L-R-D-A;

(SEQ ID NO: 22)
K-K-K-K-K-K-K-K-K-K-K-K-L-R-V-R-L-A-S-H-L-R-K-L-R-K-R-L-L-R-D-A;

(SEQ ID NO: 23)
K-K-K-K-K-K-K-K-K-K-K-K-K-K-K-K-L-R-V-R-L-A-S-H-L-R-K-L-R-K-R-L-L-R-D-A;

(SEQ ID NO: 24)
K-K-K-S-S-V-I-D-A-L-Q-Y-K-L-E-G-T-T-R-L-T-R-K-R-G-L-K-L-A-T-A-L-S-L-S-N-K-F-V-E-G-S-H;

(SEQ ID NO: 25)
K-K-K-K-K-K-K-S-S-V-I-D-A-L-Q-Y-K-L-E-G-T-T-R-L-T-R-K-R-G-L-K-L-A-T-A-L-S-L-S-N-K-F-V-E-G-S-H;

(SEQ ID NO: 26)
K-K-K-K-K-K-K-K-K-K-S-S-V-I-D-A-L-Q-Y-K-L-E-G-T-T-R-L-T-R-K-R-G-L-K-L-A-T-A-L-S-L-S-N-K-F-V-E-G-S-H;

(SEQ ID NO: 27)
K-K-K-K-K-K-K-K-K-K-K-K-K-S-S-V-I-D-A-L-Q-Y-K-L-E-G-T-T-R-L-T-R-K-R-G-L-K-L-A-T-A-L-S-L-S-N-K-F-V-E-G-S-H;
and (SEQ ID NO: 28)
K-K-K-K-K-K-K-K-K-K-K-K-K-K-K-K-S-S-V-I-D-A-L-Q-Y-K-L-E-G-T-T-R-L-T-R-K-R-G-L-K-L-A-T-A-L-S-L-S-N-K-F-V-E-G-S-H.

Further provided herein is a complex, or a pharmaceutically acceptable salt thereof, having a biologically active molecule or an imaging agent associated with a carrier peptide, as described above. In some embodiments, the biologically active molecule or imaging agent is non-covalently bound to the carrier peptide.

An imaging agent can be any chemical or substance which is used to provide the signal or contrast in imaging. For example, the imaging agent can be $^{125}$I-IgG or magnevist. A biologically active molecule can include a polypeptide; oligonucleotide; plasmid; small molecule; antibody; antibody fragment; carbohydrate; polysaccharide; lipid; glycolipid; antigen; and antigenic peptide. In some embodiments, the biologically active molecule is chosen from a: polypeptide; oligonucleotide; and plasmid. An oligonucleotide can include a coding DNA sequence; antisense DNA sequence; mRNA, antisense RNA sequence; RNAi; and siRNA. In some embodiments, the biologically active molecule is a small molecule, for example, a therapeutic agent.

The carrier peptides and complexes of carrier peptides and biologically active agents or imaging agents have various uses and can be used in various methods. For example, provided herein is a method of transporting a biologically active molecule or imaging agent across the blood-brain barrier of a subject. The method can include administering to the subject a complex, or a pharmaceutically acceptable salt thereof, having the biologically active molecule or imaging agent associated with a carrier peptide.

Also provided is a method of treating a brain disorder in a subject. The method can include administering to the subject a complex, or a pharmaceutically acceptable salt thereof, having a biologically active agent associated with a carrier peptide. The brain disorder can be chosen from meningitis, epilepsy, multiple sclerosis, neuromyelitis optica, late-stage neurological trypanosomiasis, Parkinson's, progressive multifocal leukoencephalopathy, De Vivo disease, Alzheimer's disease, HIV Encephalitis, and cancer.

This disclosure further provides a method of imaging the central nervous system of a subject. The method can include administering to the subject a complex, or a pharmaceutically acceptable salt thereof, comprising an imaging agent associated with a carrier peptide; and imaging the central nervous system of the subject.

Pharmaceutical compositions are also disclosed. A pharmaceutical composition can include a complex, or a pharmaceutically acceptable salt thereof, having a biologically active molecule or imaging agent, a carrier peptide, and a pharmaceutically acceptable carrier.

Finally, kits are also provided. A kit can include a carrier peptide. In some embodiments, the kit further includes a biologically active molecule or an imaging agent.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
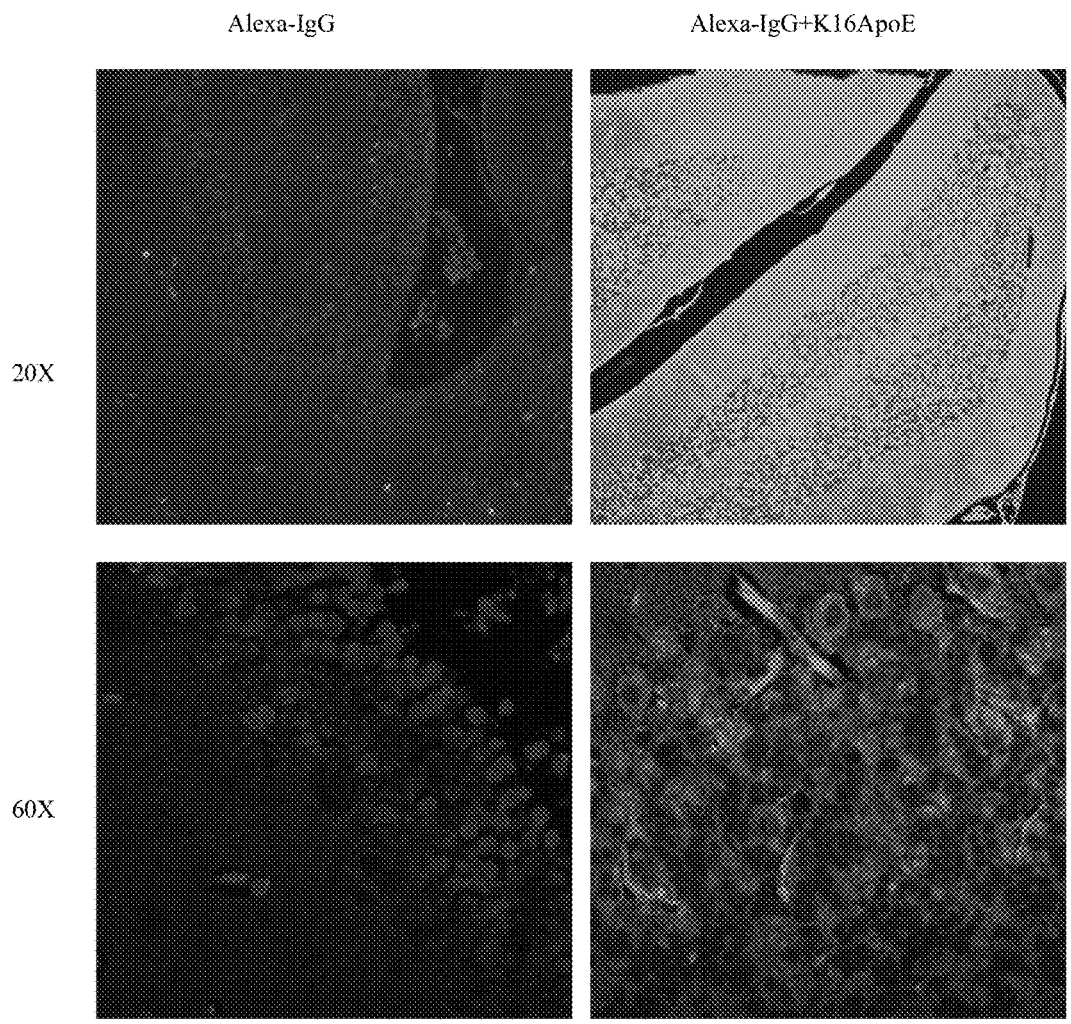
FIG. 1 is a series of images illustrating the differences between delivery of Alexa-IgG complexed to K$_{16}$ApoE (SEQ ID NO: 22) into brain and uncomplexed Alexa-IgG.

The peptides described herein can function as carrier peptides. These peptides can associate with (e.g., non-covalently bind) biologically active molecules and imaging agents to transport the biologically active molecules and imaging agents across the blood-brain barrier. In some cases, such transport may increase the effectiveness of the biological molecules and imaging agents.

Carrier Peptides

Provided herein are carrier peptides having the following sequence:

$$X_n\text{-}[B]_m$$

or a pharmaceutically acceptable salt, thereof, wherein:
X is a hydrophilic amino acid;
B is a blood-brain barrier agent;
n is an integer from 4 to 50; and
m is integer from 1 to 3.

In some embodiments, the blood-brain barrier is not L-R-K-L-R-K-R-L-L-R-L-R-K-L-R-K-R-L-L-R (SEQ ID NO: 141).

A hydrophilic amino acid can be chosen from: arginine, asparagine, aspartic acid, glutamic acid, glutamine, histidine, lysine, serine, threonine, tyrosine, and combinations and non-natural derivatives thereof. In some embodiments, a hydrophilic amino acid can be chosen from lysine or a non-natural lysine derivative, arginine or a non-natural arginine derivative, and combinations thereof. In some embodiments, the hydrophilic amino acid is lysine. Non-limiting examples of X$_n$ can include KKKK (SEQ ID NO:1); KKKKK (SEQ ID NO:2); KKKKKKKKKKKK (SEQ ID NO:3); KKKKKKKKKKKKKKK (SEQ ID NO:4); RRRR (SEQ ID NO:5); RRRRRRRR (SEQ ID NO:6); RRRRRRRRRRRR (SEQ ID NO:7); RRRRRRRRRRRRRRRR (SEQ ID NO:8); KRKR (SEQ ID NO:9); KKKR (SEQ ID NO:10); KKKRRRKKKRRR (SEQ ID NO:11); and KKKKRRRRKKKKRRRR (SEQ ID NO:12).

The variable n is an integer ranging from 4 to 50 (e.g., 4, 6, 8, 10, 12, 16, 20, 24, 26, 28, 32, 36, 40, 42, 44, 48, and 50). For example, n can range from 4 to 20. In some embodiments, n is chosen from 4, 8, 12, 16, and 20. For example, n can be 16. In some embodiments, m is 1.

A blood-brain barrier agent, as used herein, is any polypeptide or non-polypeptide ligand that can cross the blood-brain barrier. In some embodiments, a blood-brain barrier agent has a cognate receptor on brain cells or can bind to such receptors. In some embodiments, the blood-brain barrier agent comprises a transferrin-receptor binding site of a transferrin. In some embodiments, the blood-brain barrier agent comprises a receptor binding domain of an apolipoprotein. A receptor binding domain of an apolipoprotein, for example, can be chosen from the receptor binding domain of ApoA, ApoB, ApoC, ApoD, ApoE, ApoE2, ApoE3, ApoE4, and combinations thereof. In some embodiments, the receptor binding domain of an apoliprotein is chosen from the receptor binding domain of ApoB and ApoE.

In some embodiments, the blood-brain barrier agent comprises a sequence having at least 80% (e.g., at least 85%; at least 90%; at least 92%; at least 95%; at least 98%; and at least 99%) sequence identity to:

```
                                                (SEQ ID NO: 13)
L-R-V-R-L-A-S-H-L-R-K-L-R-K-R-L-L-R-D-A;

(SEQ ID NO: 14)
S-S-V-I-D-A-L-Q-Y-K-L-E-G-T-T-R-L-T-R-K-R-G-L-K-L-A-T-A-L-S-L-S-N-K-F-V-

E-G-S-H;

(SEQ ID NO: 15)
Y-P-A-K-P-E-A-P-G-E-D-A-S-P-E-E-L-S-R-Y-Y-A-S-L-R-H-Y-L-N-L-V-T-R-Q-R-Y*;

(SEQ ID NO: 16)
A-K-P-E-A-P-G-E-D-A-S-P-E-E-L-S-R-Y-Y-A-S-L-R-H-Y-L-N-L-V-T-R-Q-R-Y*;

(SEQ ID NO: 17)
Y-P-S-D-P-D-N-P-G-E-D-A-P-A-E-D-L-A-R-Y-Y-S-A-L-R-H-Y-I-N-L-I-T-R-Q-R-Y*;
or (SEQ ID NO: 18)
A-P-L-E-P-V-Y-P-G-D-D-A-T-P-E-Q-M-A-Q-Y-A-A-E-L-R-R-Y-I-N-M-L-T-R-P-R-

Y*,
``` wherein Y* is tyrosine or a tyrosine derivative (e.g., an amidated tyrosine). See, e.g., Ballantyne, G. H., *Obesity Surgery,* 16:651-658 2006.

In some embodiments, the blood-brain barrier agent includes a polypeptide comprising the following sequence:

```
                                (SEQ ID NO: 29)
L-R-XI-R-X2-X3-X4-H-L-R-X5-X6-X7-K-R-L-X8-R-D-X9
``` wherein:

X1 is selected from the group consisting of A, L, S, and V;
X2 is selected from the group consisting of L and M;
X3 is selected from the group consisting of A and S;
X4 is selected from the group consisting of N, S, and T;
X5 is selected from the group consisting of K and N;
X6 is selected from the group consisting of L, M, and V;
X7 is selected from the group consisting of R and P;
X8 is selected from the group consisting of L and M; and
X9 is selected from the group consisting of A and L.

Non-limiting examples of a blood-brain barrier agents according to this sequence include:

```
                                (SEQ ID NO: 13)
L-R-V-R-L-A-S-H-L-R-K-L-R-K-R-L-L-R-D-A;

(SEQ ID NO: 30)
L-R-S-R-L-A-S-H-L-R-K-L-R-K-R-L-L-R-D-A;

(SEQ ID NO: 31)
L-R-V-R-M-A-S-H-L-R-K-L-R-K-R-L-L-R-D-A;

(SEQ ID NO: 32)
L-R-V-R-L-A-T-H-L-R-K-L-R-K-R-L-L-R-D-A;
```

-continued

```
                                (SEQ ID NO: 33)
L-R-V-R-L-A-S-H-L-R-K-L-P-K-R-L-L-R-D-A;

(SEQ ID NO: 34)
L-R-V-R-L-A-S-H-L-R-K-L-R-K-R-L-M-R-D-A;

(SEQ ID NO: 35)
L-R-V-R-L-A-S-H-L-R-N-L-R-K-R-L-L-R-D-A;

(SEQ ID NO: 36)
L-R-V-R-L-A-S-H-L-R-K-V-R-K-R-L-L-R-D-A;
```

-continued

```
                                (SEQ ID NO: 37)
L-R-V-R-M-S-S-H-L-R-K-L-R-K-R-L-L-R-D-A;

(SEQ ID NO: 38)
L-R-V-R-L-A-S-H-L-R-N-V-R-K-R-L-L-R-D-A;

(SEQ ID NO: 39)
L-R-V-R-L-A-S-H-L-R-N-M-R-K-R-L-L-R-D-A;

(SEQ ID NO: 40)
L-R-A-R-M-A-S-H-L-R-K-L-R-K-R-L-L-R-D-A;

(SEQ ID NO: 41)
L-R-V-R-L-S-S-H-L-R-K-L-R-K-R-L-M-R-D-A;

(SEQ ID NO: 42)
L-R-S-R-L-A-S-H-L-R-K-L-R-K-R-L-M-R-D-A;

(SEQ ID NO: 43)
L-R-V-R-L-S-S-H-L-P-K-L-R-K-R-L-L-R-D-A;

(SEQ ID NO: 44)
L-R-V-R-L-A-S-H-L-R-K-M-R-K-R-L-M-R-D-A;

(SEQ ID NO: 45)
L-R-V-R-L-A-S-H-L-R-N-L-P-K-R-L-L-R-D-A;

(SEQ ID NO: 129)
L-R-L-R-L-A-S-H-L-R-K-L-R-K-R-L-L-R-D-L;
and (SEQ ID NO: 130)
L-R-V-R-L-A-N-H-L-R-K-L-R-K-R-L-L-R-D-L.
```

In some embodiments, the blood-brain barrier agent is less than 100 amino acids in length (e.g., less than 90 amino acids in length; less than 80 amino acids in length; less than 75 amino acids in length; less than 70 amino acids in length; less than 65 amino acids in length; less than 62 amino acids in length; less than 60 amino acids in length; less than 55 amino acids in length; less than 50 amino acids in length; and less than 45 amino acids in length).

"Percent sequence identity" refers to the degree of sequence identity between any given reference sequence, e.g., SEQ ID NO:13, and a candidate blood-brain barrier agent sequence. A candidate sequence typically has a length that is from 80 percent to 200 percent of the length of the reference sequence (e.g., 82, 85, 87, 89, 90, 93, 95, 97, 99, 100, 105, 110, 115, 120, 130, 140, 150, 160, 170, 180, 190, or 200 percent of the length of the reference sequence). A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10; gap extension penalty: 5.0; and weight transitions: yes. For fast pairwise alignment of peptide sequences, the following parameters are used: word size: 1; window size: 5; scoring method: percentage; number of top diagonals: 5; gap penalty: 3. For multiple alignment of peptide sequences, the following parameters are used: weight matrix: blosum; gap opening penalty: 10; gap extension penalty: 0.5; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The variable m is an integer from 1 to 3. In some embodiments, m is 1.

In some embodiments, a carrier peptide can be chosen from:

```
                                                          (SEQ ID NO: 19)
K-K-K-K-L-R-V-R-L-A-S-H-L-R-K-L-R-K-R-L-L-R-D-A;

(SEQ ID NO: 20)
K-K-K-K-K-K-K-L-R-V-R-L-A-S-H-L-R-K-L-R-K-R-L-L-R-D-A;

(SEQ ID NO: 21)
K-K-K-K-K-K-K-K-K-K-L-R-V-R-L-A-S-H-L-R-K-L-R-K-R-L-L-R-D-A;

(SEQ ID NO: 22)
K-K-K-K-K-K-K-K-K-K-K-K-K-L-R-V-R-L-A-S-H-L-R-K-L-R-K-R-L-L-R-D-

A;

(SEQ ID NO: 23)
K-K-K-K-K-K-K-K-K-K-K-K-K-K-K-K-L-R-V-R-L-A-S-H-L-R-K-L-R-K-R-

L-L-R-D-A;

(SEQ ID NO: 24)
K-K-K-K-S-S-V-I-D-A-L-Q-Y-K-L-E-G-T-T-R-L-T-R-K-R-G-L-K-L-A-T-A-L-S-L-S-N-

K-F-V-E-G-S-H;

(SEQ ID NO: 25)
K-K-K-K-K-K-K-S-S-V-I-D-A-L-Q-Y-K-L-E-G-T-T-R-L-T-R-K-R-G-L-K-L-A-T-A-

L-S-L-S-N-K-F-V-E-G-S-H;

(SEQ ID NO: 26)
K-K-K-K-K-K-K-K-K-K-S-S-V-I-D-A-L-Q-Y-K-L-E-G-T-T-R-L-T-R-K-R-G-L-K-

L-A-T-A-L-S-L-S-N-K-F-V-E-G-S-H;

(SEQ ID NO: 27)
K-K-K-K-K-K-K-K-K-K-K-K-K-S-S-V-I-D-A-L-Q-Y-K-L-E-G-T-T-R-L-T-R-K-

R-G-L-K-L-A-T-A-L-S-L-S-N-K-F-V-E-G-S-H;
and
```

(SEQ ID NO: 28)
K-K-K-K-K-K-K-K-K-K-K-K-K-K-K-K-K-K-K-S-S-V-I-D-A-L-Q-Y-K-L-E-G-T-T-R-L-T-R-K-R-G-L-K-L-A-T-A-L-S-L-S-N-K-F-V-E-G-S-H.

In some embodiments, a carrier peptide can be chosen from:

(SEQ ID NO: 142)
[X]$_n$-L-R-X1-R-X2-X3-X4-H-L-R-X5-X6-X7-K-R-L-X8-R-D-X9 wherein:
X is a hydrophilic amino acid;
n is an integer from 4 to 20;
X1 is selected from the group consisting of A, L, S, and V;
X2 is selected from the group consisting of L and M;
X3 is selected from the group consisting of A and S;
X4 is selected from the group consisting of N, S, and T;
X5 is selected from the group consisting of K and N;
X6 is selected from the group consisting of L, M, and V;
X7 is selected from the group consisting of R and P;
X8 is selected from the group consisting of L and M; and
X9 is selected from the group consisting of A and L.

Non-limiting examples of a blood-brain barrier agents according to this sequence include:

(SEQ ID NO: 19)
K-K-K-K-L-R-V-R-L-A-S-H-L-R-K-L-R-K-R-L-L-R-D-A;

(SEQ ID NO: 20)
K-K-K-K-K-K-K-K-L-R-V-R-L-A-S-H-L-R-K-L-R-K-R-L-L-R-D-A;

(SEQ ID NO: 21)
K-K-K-K-K-K-K-K-K-K-K-K-L-R-V-R-L-A-S-H-L-R-K-L-R-K-R-L-L-R-D-A;

(SEQ ID NO: 22)
K-K-K-K-K-K-K-K-K-K-K-K-K-K-K-K-L-R-V-R-L-A-S-H-L-R-K-L-R-K-R-L-L-R-D-A;

(SEQ ID NO: 23)
K-K-K-K-K-K-K-K-K-K-K-K-K-K-K-K-K-K-K-K-L-R-V-R-L-A-S-H-L-R-K-L-R-K-R-L-L-R-D-A;

(SEQ ID NO: 46)
K-K-K-K-L-R-S-R-L-A-S-H-L-R-K-L-R-K-R-L-L-R-D-A;

(SEQ ID NO: 47)
K-K-K-K-K-K-K-K-L-R-S-R-L-A-S-H-L-R-K-L-R-K-R-L-L-R-D-A;

(SEQ ID NO: 48)
K-K-K-K-K-K-K-K-K-K-K-K-L-R-S-R-L-A-S-H-L-R-K-L-R-K-R-L-L-R-D-A;

(SEQ ID NO: 49)
K-K-K-K-K-K-K-K-K-K-K-K-K-K-K-K-L-R-S-R-L-A-S-H-L-R-K-L-R-K-R-L-L-R-D-A;

(SEQ ID NO: 50)
K-K-K-K-K-K-K-K-K-K-K-K-K-K-K-K-K-K-K-K-L-R-S-R-L-A-S-H-L-R-K-L-R-K-R-L-L-R-D-A;

(SEQ ID NO: 51)
K-K-K-K-L-R-V-R-M-A-S-H-L-R-K-L-R-K-R-L-L-R-D-A;

(SEQ ID NO: 52)
K-K-K-K-K-K-K-K-L-R-V-R-M-A-S-H-L-R-K-L-R-K-R-L-L-R-D-A;

(SEQ ID NO: 53)
K-K-K-K-K-K-K-K-K-K-K-K-L-R-V-R-M-A-S-H-L-R-K-L-R-K-R-L-L-R-D-A;

(SEQ ID NO: 54)
K-K-K-K-K-K-K-K-K-K-K-K-K-K-K-K-L-R-V-R-M-A-S-H-L-R-K-L-R-K-R-L-L-R-D-A;

-continued (SEQ ID NO: 55)
K-K-K-K-K-K-K-K-K-K-K-K-K-K-K-K-K-L-R-V-R-M-A-S-H-L-R-K-L-R-K-R-L-L-R-D-A;

(SEQ ID NO: 56)
K-K-K-L-R-V-R-L-A-T-H-L-R-K-L-R-K-R-L-L-R-D-A;

(SEQ ID NO: 57)
K-K-K-K-K-K-L-R-V-R-L-A-T-H-L-R-K-L-R-K-R-L-L-R-D-A;

(SEQ ID NO: 58)
K-K-K-K-K-K-K-K-K-L-R-V-R-L-A-T-H-L-R-K-L-R-K-R-L-L-R-D-A;

(SEQ ID NO: 59)
K-K-K-K-K-K-K-K-K-K-K-K-L-R-V-R-L-A-T-H-L-R-K-L-R-K-R-L-L-R-D-A;

(SEQ ID NO: 60)
K-K-K-K-K-K-K-K-K-K-K-K-K-K-K-K-L-R-V-R-L-A-T-H-L-R-K-L-R-K-R-L-L-R-D-A;

(SEQ ID NO: 61)
K-K-K-L-R-V-R-L-A-S-H-L-R-K-L-P-K-R-L-L-R-D-A;

(SEQ ID NO: 62)
K-K-K-K-K-K-L-R-V-R-L-A-S-H-L-R-K-L-P-K-R-L-L-R-D-A;

(SEQ ID NO: 63)
K-K-K-K-K-K-K-K-K-L-R-V-R-L-A-S-H-L-R-K-L-P-K-R-L-L-R-D-A;

(SEQ ID NO: 64)
K-K-K-K-K-K-K-K-K-K-K-K-L-R-V-R-L-A-S-H-L-R-K-L-P-K-R-L-L-R-D-A;

(SEQ ID NO: 65)
K-K-K-K-K-K-K-K-K-K-K-K-K-K-K-K-L-R-V-R-L-A-S-H-L-R-K-L-P-K-R-L-L-R-D-A;

(SEQ ID NO: 66)
K-K-K-L-R-V-R-L-A-S-H-L-R-K-L-R-K-R-L-M-R-D-A;

(SEQ ID NO: 67)
K-K-K-K-K-K-L-R-V-R-L-A-S-H-L-R-K-L-R-K-R-L-M-R-D-A;

(SEQ ID NO: 68)
K-K-K-K-K-K-K-K-K-L-R-V-R-L-A-S-H-L-R-K-L-R-K-R-L-M-R-D-A;

(SEQ ID NO: 69)
K-K-K-K-K-K-K-K-K-K-K-K-L-R-V-R-L-A-S-H-L-R-K-L-R-K-R-L-M-R-D-A;

(SEQ ID NO: 70)
K-K-K-K-K-K-K-K-K-K-K-K-K-K-K-K-L-R-V-R-L-A-S-H-L-R-K-L-R-K-R-L-M-R-D-A;

(SEQ ID NO: 71)
K-K-K-L-R-V-R-L-A-S-H-L-R-N-L-R-K-R-L-L-R-D-A;

(SEQ ID NO: 72)
K-K-K-K-K-K-L-R-V-R-L-A-S-H-L-R-N-L-R-K-R-L-L-R-D-A;

(SEQ ID NO: 73)
K-K-K-K-K-K-K-K-K-L-R-V-R-L-A-S-H-L-R-N-L-R-K-R-L-L-R-D-A;

(SEQ ID NO: 74)
K-K-K-K-K-K-K-K-K-K-K-K-L-R-V-R-L-A-S-H-L-R-N-L-R-K-R-L-L-R-D-A;

(SEQ ID NO: 75)
K-K-K-K-K-K-K-K-K-K-K-K-K-K-K-K-L-R-V-R-L-A-S-H-L-R-N-L-R-K-R-L-L-R-D-A;

-continued (SEQ ID NO: 76)
K-K-K-K-L-R-V-R-L-A-S-H-L-R-K-V-R-K-R-L-L-R-D-A;

(SEQ ID NO: 77)
K-K-K-K-K-K-L-R-V-R-L-A-S-H-L-R-K-V-R-K-R-L-L-R-D-A;

(SEQ ID NO: 78)
K-K-K-K-K-K-K-K-L-R-V-R-L-A-S-H-L-R-K-V-R-K-R-L-L-R-D-A;

(SEQ ID NO: 79)
K-K-K-K-K-K-K-K-K-K-K-K-L-R-V-R-L-A-S-H-L-R-K-V-R-K-R-L-L-R-D-A;

(SEQ ID NO: 80)
K-K-K-K-K-K-K-K-K-K-K-K-K-K-K-K-L-R-V-R-L-A-S-H-L-R-K-V-R-K-R-L-L-R-D-A;

(SEQ ID NO: 81)
K-K-K-K-L-R-V-R-M-S-S-H-L-R-K-L-R-K-R-L-L-R-D-A;

(SEQ ID NO: 82)
K-K-K-K-K-K-L-R-V-R-M-S-S-H-L-R-K-L-R-K-R-L-L-R-D-A;

(SEQ ID NO: 83)
K-K-K-K-K-K-K-K-K-K-L-R-V-R-M-S-S-H-L-R-K-L-R-K-R-L-L-R-D-A;

(SEQ ID NO: 84)
K-K-K-K-K-K-K-K-K-K-K-K-K-L-R-V-R-M-S-S-H-L-R-K-L-R-K-R-L-L-R-D-A;

(SEQ ID NO: 85)
K-K-K-K-K-K-K-K-K-K-K-K-K-K-K-K-K-L-R-V-R-M-S-S-H-L-R-K-L-R-K-R-L-L-R-D-A;

(SEQ ID NO: 86)
K-K-K-K-L-R-V-R-L-A-S-H-L-R-N-V-R-K-R-L-L-R-D-A;

(SEQ ID NO: 87)
K-K-K-K-K-K-K-L-R-V-R-L-A-S-H-L-R-N-V-R-K-R-L-L-R-D-A;

(SEQ ID NO: 88)
K-K-K-K-K-K-K-K-K-K-L-R-V-R-L-A-S-H-L-R-N-V-R-K-R-L-L-R-D-A;

(SEQ ID NO: 89)
K-K-K-K-K-K-K-K-K-K-K-K-K-L-R-V-R-L-A-S-H-L-R-N-V-R-K-R-L-L-R-D-A;

(SEQ ID NO: 90)
K-K-K-K-K-K-K-K-K-K-K-K-K-K-K-K-K-L-R-V-R-L-A-S-H-L-R-N-V-R-K-R-L-L-R-D-A;

(SEQ ID NO: 91)
K-K-K-K-L-R-V-R-L-A-S-H-L-R-N-M-R-K-R-L-L-R-D-A;

(SEQ ID NO: 92)
K-K-K-K-K-K-K-L-R-V-R-L-A-S-H-L-R-N-M-R-K-R-L-L-R-D-A;

(SEQ ID NO: 93)
K-K-K-K-K-K-K-K-K-K-L-R-V-R-L-A-S-H-L-R-N-M-R-K-R-L-L-R-D-A;

(SEQ ID NO: 94)
K-K-K-K-K-K-K-K-K-K-K-K-K-L-R-V-R-L-A-S-H-L-R-N-M-R-K-R-L-L-R-D-A;

(SEQ ID NO: 95)
K-K-K-K-K-K-K-K-K-K-K-K-K-K-K-K-K-L-R-V-R-L-A-S-H-L-R-N-M-R-K-R-L-L-R-D-A;

(SEQ ID NO: 96)
K-K-K-L-R-A-R-M-A-S-H-L-R-K-L-R-K-R-L-L-R-D-A;

(SEQ ID NO: 97)
K-K-K-K-K-K-K-L-R-A-R-M-A-S-H-L-R-K-L-R-K-R-L-L-R-D-A;

```
                                                       (SEQ ID NO: 98)
K-K-K-K-K-K-K-K-K-K-L-R-A-R-M-A-S-H-L-R-K-L-R-K-R-L-L-R-D-A;

(SEQ ID NO: 99)
K-K-K-K-K-K-K-K-K-K-K-K-K-L-R-A-R-M-A-S-H-L-R-K-L-R-K-R-L-L-R-
D-A;

(SEQ ID NO: 100)
K-K-K-K-K-K-K-K-K-K-K-K-K-K-K-K-K-L-R-A-R-M-A-S-H-L-R-K-L-R-K-
R-L-L-R-D-A;

(SEQ ID NO: 101)
K-K-K-K-L-R-V-R-L-S-S-H-L-R-K-L-R-K-R-L-M-R-D-A;

(SEQ ID NO: 102)
K-K-K-K-K-K-L-R-V-R-L-S-S-H-L-R-K-L-R-K-R-L-M-R-D-A;

(SEQ ID NO: 103)
K-K-K-K-K-K-K-K-K-K-L-R-V-R-L-S-S-H-L-R-K-L-R-K-R-L-M-R-D-A;

(SEQ ID NO: 104)
K-K-K-K-K-K-K-K-K-K-K-K-K-L-R-V-R-L-S-S-H-L-R-K-L-R-K-R-L-M-R-D-
A;

(SEQ ID NO: 105)
K-K-K-K-K-K-K-K-K-K-K-K-K-K-K-K-K-L-R-V-R-L-S-S-H-L-R-K-L-R-K-R-
L-M-R-D-A;

(SEQ ID NO: 106)
K-K-K-L-R-S-R-L-A-S-H-L-R-K-L-R-K-R-L-M-R-D-A;

(SEQ ID NO: 107)
K-K-K-K-K-K-L-R-S-R-L-A-S-H-L-R-K-L-R-K-R-L-M-R-D-A;

(SEQ ID NO: 108)
K-K-K-K-K-K-K-K-K-K-L-R-S-R-L-A-S-H-L-R-K-L-R-K-R-L-M-R-D-A;

(SEQ ID NO: 109)
K-K-K-K-K-K-K-K-K-K-K-K-K-L-R-S-R-L-A-S-H-L-R-K-L-R-K-R-L-M-R-D-
A;

(SEQ ID NO: 110)
K-K-K-K-K-K-K-K-K-K-K-K-K-K-K-K-K-L-R-S-R-L-A-S-H-L-R-K-L-R-K-R-
L-M-R-D-A;

(SEQ ID NO: 111)
K-K-K-L-R-V-R-L-S-S-H-L-P-K-L-R-K-R-L-L-R-D-A;

(SEQ ID NO: 112)
K-K-K-K-K-K-L-R-V-R-L-S-S-H-L-P-K-L-R-K-R-L-L-R-D-A;

(SEQ ID NO: 113)
K-K-K-K-K-K-K-K-K-K-L-R-V-R-L-S-S-H-L-P-K-L-R-K-R-L-L-R-D-A;

(SEQ ID NO: 114)
K-K-K-K-K-K-K-K-K-K-K-K-K-L-R-V-R-L-S-S-H-L-P-K-L-R-K-R-L-L-R-D-
A;

(SEQ ID NO: 115)
K-K-K-K-K-K-K-K-K-K-K-K-K-K-K-K-K-L-R-V-R-L-S-S-H-L-P-K-L-R-K-R-
L-L-R-D-A;

(SEQ ID NO: 116)
K-K-K-K-L-R-V-R-L-A-S-H-L-R-K-M-R-K-R-L-M-R-D-A;

(SEQ ID NO: 117)
K-K-K-K-K-K-L-R-V-R-L-A-S-H-L-R-K-M-R-K-R-L-M-R-D-A;

(SEQ ID NO: 118)
K-K-K-K-K-K-K-K-K-K-L-R-V-R-L-A-S-H-L-R-K-M-R-K-R-L-M-R-D-A;
```

```
                                                         (SEQ ID NO: 119)
K-K-K-K-K-K-K-K-K-K-K-K-K-K-L-R-V-R-L-A-S-H-L-R-K-M-R-K-R-L-M-R-
D-A;

(SEQ ID NO: 120)
K-K-K-K-K-K-K-K-K-K-K-K-K-K-K-K-K-L-R-V-R-L-A-S-H-L-R-K-M-R-K-
R-L-M-R-D-A;

(SEQ ID NO: 121)
K-K-K-K-L-R-V-R-L-A-S-H-L-R-N-L-P-K-R-L-L-R-D-A;

(SEQ ID NO: 122)
K-K-K-K-K-K-L-R-V-R-L-A-S-H-L-R-N-L-P-K-R-L-L-R-D-A;

(SEQ ID NO: 123)
K-K-K-K-K-K-K-K-K-K-L-R-V-R-L-A-S-H-L-R-N-L-P-K-R-L-L-R-D-A;

(SEQ ID NO: 124)
K-K-K-K-K-K-K-K-K-K-K-K-K-L-R-V-R-L-A-S-H-L-R-N-L-P-K-R-L-L-R-D-
A;

(SEQ ID NO: 125)
K-K-K-K-K-K-K-K-K-K-K-K-K-K-K-K-K-L-R-V-R-L-A-S-H-L-R-N-L-P-K-R-
L-L-R-D-A;

(SEQ ID NO: 131)
K-K-K-L-R-L-R-L-A-S-H-L-R-K-L-R-K-R-L-L-R-D-L;

(SEQ ID NO: 132)
K-K-K-K-K-K-L-R-L-R-L-A-S-H-L-R-K-L-R-K-R-L-L-R-D-L;

(SEQ ID NO: 133)
K-K-K-K-K-K-K-K-K-L-R-L-R-L-A-S-H-L-R-K-L-R-K-R-L-L-R-D-L;

(SEQ ID NO: 134)
K-K-K-K-K-K-K-K-K-K-K-K-L-R-L-R-L-A-S-H-L-R-K-L-R-K-R-L-L-R-D-
L;

(SEQ ID NO: 135)
K-K-K-K-K-K-K-K-K-K-K-K-K-K-K-L-R-L-R-L-A-S-H-L-R-K-L-R-K-R-
L-L-R-D-L;

(SEQ ID NO: 136)
K-K-K-K-L-R-V-R-L-A-N-H-L-R-K-L-R-K-R-L-L-R-D-L;

(SEQ ID NO: 137)
K-K-K-K-K-K-L-R-V-R-L-A-N-H-L-R-K-L-R-K-R-L-L-R-D-L;

(SEQ ID NO: 138)
K-K-K-K-K-K-K-K-K-L-R-V-R-L-A-N-H-L-R-K-L-R-K-R-L-L-R-D-L;

(SEQ ID NO: 139)
K-K-K-K-K-K-K-K-K-K-K-K-L-R-V-R-L-A-N-H-L-R-K-L-R-K-R-L-L-R-D-
L;

(SEQ ID NO: 140)
K-K-K-K-K-K-K-K-K-K-K-K-K-K-K-L-R-V-R-L-A-N-H-L-R-K-L-R-K-
R-L-L-R-D-L.
```

Complexes

Also provided herein are complexes having a biologically active molecule or an imaging agent associated with a carrier peptide as described herein. In some embodiments, the biologically active molecule or imaging agent is non-covalently bound to the carrier peptide.

As used herein, a "biologically active molecule" includes any molecule which, if transported across the blood-brain barrier, can have a biological effect. Examples of biologically active molecules include polypeptides, which include functional domains of biologically active molecules, particular examples include growth factors, enzymes, transcription factors, toxins, antigenic peptides (as for vaccines), antibodies, and antibody fragments. For example, brain derived neurotrophic factor, fibroblast growth factor (e.g., (FGF)-2 or multiple FGFs), nerve growth factor, neurotrophin (e.g., NT-3 and NT-4/5), glial derived neurotrophic factor, ciliary neurotrophic factor, neurturin, neuregulins, interleukins, transforming growth factor (e.g., TGF-α and TGF-β), vasoactibe intestinal peptide, epidermal growth factor (EGF), erythropoietin, heptocytel growth factor, platelet derived growth factor, artemin, persephin, netrins, cardiotrophin-1, stem cell factor, midkine, pleiotrophin, bone morphogenic proteins, saposins, semaporins, leukemia inhibitory factor, anti-Aβ, anti-HER2, anti-EGF, anti-nogo A, anti-TRAIL (tumor necrosis factor-related apoptosis-inducing ligand), anti-α-synuclein, anti-htt, anti-prion, anti-West Nile virus, αL-iduronidase, iduronate-2-sulfatase, N-acetyl-galactosamine-6-sulfatase, arylsulfatase B, acid α-glucosidase, and acid sphingomyelinase (See, Pardridge, W. M., *Bioconjug. Chem.* 19(7): 1327-38 2008). Additional examples of biologically active molecules include oligonucleotides, such as natural or engineered plasmids, coding DNA sequences, antisense DNA sequences, mRNAs, antisense RNA sequences, RNAis, and siRNAs; carbohydrates; lipids; and glycolipids.

Further examples of biologically active molecules include small molecules, including therapeutic agents, in particular those with low blood-brain barrier permeability. Some examples of these therapeutic agents include cancer drugs, such as daunorubicin and toxic chemicals which, because of the lower dosage that can be administered by this method, can now be more safely administered. For example, a therapeutic agent can include bevacizumab, irinotecan, zoledronate, and temozolomide.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl.

Numerous other examples of biologically active molecules will be apparent to the skilled artisan.

Yet another example of a biologically active molecule is an antigenic peptide. Antigenic peptides can be administered to provide immunological protection when imported by cells involved in the immune response. Other examples include immunosuppressive peptides (e.g., peptides that block autoreactive T cells, which peptides are known in the art).

Polypeptides from a few amino acids to about a thousand amino acids can be used. In some embodiments, the size range for polypeptides is from a few amino acids to about 250 amino acids (e.g., about 3 to about 250 amino acids; about 20 to about 250 amino acids; about 50 to about 250 amino acids; about 100 to about 250 amino acids; about 150 to about 250 amino acids; about 3 amino acids to about 200 amino acids; about 3 amino acids to about 150 amino acids; about 3 amino acids to about 175 amino acids; about 3 amino acids to about 125 amino acids; about 25 amino acids to about 200 amino acids; about 50 amino acids to about 150 amino acids; and about 75 amino acids to about 225 amino acids). For any molecule, size ranges can be up to about a molecular weight of about 1 million. In some embodiments, the size ranges up to a molecular weight of about 25,000, and in particular embodiments, the size ranges can be up to a molecular weight of about 3,000.

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004; Agrawal et al., U.S. Pat. No. 5,591,721; Agrawal, U.S. Pat. No. 5,652,356). Typically, antisense molecules will be complementary to a target sequence along a single contiguous sequence of the antisense molecule. However, in certain embodiments, an antisense molecule may bind to a substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

RNA interference (RNAi) and short intervening RNA (siRNA) sequences can be used to modulate (e.g., inhibit) gene expression (see, e.g., Elbashir et al., 2001, Nature, 411, 494 498; and Bass, 2001, Nature, 411, 428 429; Bass, 2001, Nature, 411, 428 429; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914). In one embodiment, a siRNA molecule comprises a double stranded RNA wherein one strand of the RNA is complimentary to the RNA of interest. In another embodiment, a siRNA molecule comprises a double stranded RNA wherein one strand of the RNA comprises a portion of a sequence of an RNA of interest. In yet another embodiment, a siRNA molecule of the invention comprises a double stranded RNA wherein both strands of RNA are connected by a non-nucleotide linker. Alternately, a siRNA molecule of the invention comprises a double stranded RNA wherein both strands of RNA are connected by a nucleotide linker, such as a loop or stem loop structure.

The term "antibody" as used herein refers to immunoglobulin molecules and immunologically active portions of immunoglobulin molecules (i.e., molecules that contain an antigen binding site that specifically binds to a peptide). An antibody can be a monoclonal antibody, a polyclonal antibody, a humanized antibody, a fully human antibody, a single chain antibody, a chimeric antibody, or a fragment thereof. The term "antibody fragment" of a full length antibody refers to one or more fragments of a full-length antibody that retain the ability to specifically bind to a target of interest.

An imaging agent, as used herein, can be any chemical or substance which is used to provide the signal or contrast in imaging. The signal enhancing domain can be an organic molecule, metal ion, salt or chelate, particle (particularly iron particle), or labeled peptide, protein, polymer or liposome.

In some embodiments, the imaging agent is a physiologically compatible metal chelate compound consisting of one or more cyclic or acyclic organic chelating agents complexed to one or more metal ions with atomic numbers 21-29, 42, 44, or 57-83.

For x-ray imaging, the imaging agent may consist of iodinated organic molecules or chelates of heavy metal ions of atomic numbers 57 to 83. In some embodiments, the imaging agent is $^{125}$I-IgG. Examples of suitable compounds are described in M. Sovak, ed., "Radiocontrast Agents," *Springer-Verlag*, pp. 23-125 (1984) and U.S. Pat. No. 4,647, 447.

For ultrasound imaging, the imaging agent can consist of gas-filled bubbles such as Albunex, Echovist, or Levovist, or particles or metal chelates where the metal ions have atomic numbers 21-29, 42, 44 or 57-83. Examples of suitable compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87. (1990).

For nuclear radiopharmaceutical imaging or radiotherapy, the imaging agent can consist of a radioactive molecule. In some embodiments, the chelates of Tc, Re, Co, Cu, Au, Ag, Pb, Bi, In, and Ga can be used. In some embodiments, the chelates of Tc-99m can be used. Examples of suitable compounds are described in Rayudu G V S, *Radiotracers for Medical Applications*, I, pp. 201 and D. P. Swanson et al., ed., *Pharmaceuticals in Medical Imaging*, pp. 279-644 (1990).

For ultraviolet/visible/infrared light imaging, the imaging agent can consist of any organic or inorganic dye or any metal chelate.

For MRI, the imaging agent can consist of a metal-ligand complex of a paramagnetic form of a metal ion with atomic numbers 21-29, 42, 44, or 57-83. In some embodiments, the paramagnetic metal is chosen from: Gd(III), Fe(III), Mn(II and III), Cr(III), Cu(II), Dy(III), Tb(III), Ho(III), Er(III) and Eu(III). Many suitable chelating ligands for MRI agents are known in the art. These can also be used for metal chelates for other forms of biological imaging. For example, an imaging agent can include:

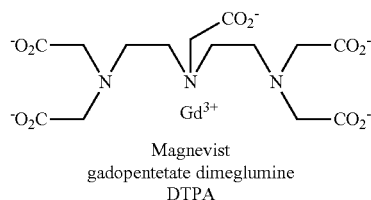

Magnevist
gadopentetate dimeglumine
DTPA

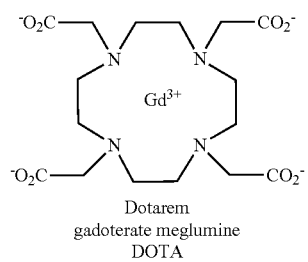

Dotarem
gadoterate meglumine
DOTA

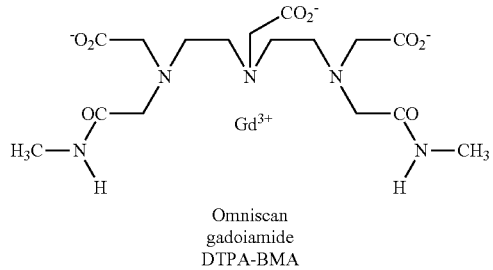

Omniscan
gadoiamide
DTPA-BMA

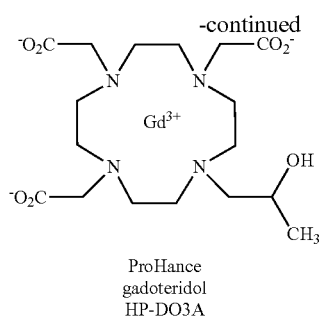

ProHance
gadoteridol
HP-DO3A

"Associated with", as used herein, is meant that the biologically active molecule or imaging agent is conjugated to the carrier peptide in such a manner that when the carrier peptide crosses the blood-brain barrier, the molecule or agent is also imported. In certain embodiments, the biologically active molecule or imaging agent is non-covalently bound to the carrier peptide. For example, the biologically active molecule and the carrier peptide may be associated through electrostatic interactions. In other embodiments, the carrier peptide may be covalently bound, either directly or indirectly (e.g., through a linker), to the biologically active molecule or imaging agent.

A linker can be any moiety suitable for linking a carrier peptide to a biologically active molecule. A linker can be bound at the C-terminus, the N-terminus, or both, of a carrier peptide. Additionally, a linker can be bound to the side chain of a carrier peptide. If a carrier peptide is bound to multiple linkers, each linker can be different. A linker can be covalently linked to a side chain of an amino acid, e.g., lysine, glutamine, cysteine, methionine, glutamate, aspartate, asparagine.

In some embodiments an amino acid side chain can serve as the linker. For example the epsilon amino group ($\epsilon$-NH$_2$) can be used to conjugate to a carrier for instance through an amide or thiourea linkage. Similarly the delta amino group of ornithine (orn), the gamma amino group of diaminobutyric acid (dab), or the beta amino group of diamino proprionic acid (dpr) can also act as linkers. These amino acids may be at the C- or N-terminus of the carrier peptide or they may be positioned within the carrier peptide sequence.

The complex composed of a biologically active molecule or imaging agent and a carrier peptide can be prepared by any method known by those having ordinary skill in the art. In some embodiments, the carrier peptide and the biologically active molecule or imaging agent are combined, incubated at room temperature, and then used. For example, solutions can be prepared of the delivery peptide (K16ApoE (SEQ ID NO: 22)) and IgG in PBS (phosphate buffered saline) or OptiMem (commercially available) or cell culture media without serum in desired concentrations. The delivery peptide and IgG can be mixed in the desired ratios and then incubated at room temperature for 30-60 minute. Following incubation, the mixture is ready for injection/delivery.

Combinations of the biologically active molecule and the carrier peptide can be prepared at a variety of molar ratios. For example, a molar ratio of biologically active molecule to carrier peptide can range from about 1:1 to about 1:200 (e.g., 1:2; 1:5; 1:8; 1:10; 1:25; 1:30; 1:40; 1:45; 1:50; 1:60; 1:65; 1:70; 1:75; 1:80; 1:90; 1:100; 1:125; 1:135; 1:145; 1:150; 1:175; and 1:190). In some embodiments, a molar excess of carrier peptide to biologically active molecule is used. For example, the molar ratio of biologically active molecule to carrier peptide can range from about 1:20 to about 1:100 (e.g, 1:50 to about 1:90). In some cases, the ratio can be 1:70.

The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of compounds described herein. In general the useful properties of the compounds described herein do not depend critically on whether the compound is or is not in a salt form, so unless clearly indicated otherwise (such as specifying that the compound should be in "free base" or "free acid" form), reference in the specification to a carrier peptide or a complex comprising a carrier peptide should be understood as encompassing salt forms of the compound, whether or not this is explicitly stated.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding carrier peptide or complex by reacting, for example, the appropriate acid or base with a carrier peptide or complex as described herein. Preferably the salts are in crystalline form, and preferably prepared by crystallization of the salt from a suitable solvent. A person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

Methods of Use

Also provided herein are methods of using carrier peptides to transport a biologically active molecule or imaging agent across the blood-brain barrier of a subject. The method can include administering to the subject a complex having a biologically active molecule or imaging agent associated with a carrier peptide, or a pharmaceutically acceptable salt, as described herein.

A subject can include both mammals and non-mammals. Mammals include, for example, humans; nonhuman primates, e.g. apes and monkeys; cattle; horses; sheep; rats; mice; pigs; and goats. Non-mammals include, for example, fish and birds.

Transporting a biologically active molecule can include importing the molecule across the blood-brain barrier.

Further provided herein is a method of treating a brain disorder in a subject. The method can include administering to the subject a complex comprising a biologically active agent associated with a carrier peptide, as described herein. In some embodiments, the biologically active molecule is a therapeutic agent. In some embodiments, the brain disorder is chosen from: meningitis, epilepsy, multiple sclerosis, neuromyelitis optica, late-stage neurological trypanosomiasis, Parkinson's, progressive multifocal leukoencephalopathy, De Vivo disease, Alzheimer's disease, HIV Encephalitis, and cancer.

In some embodiments, the brain disorder is a brain cancer, for example astrocytoma, medulloblastoma, glioma, ependymoma, germinoma (pinealoma), glioblastoma multiform, oligodendroglioma, schwannoma, retinoblastoma, and congenital tumors; or a cancer of the spinal cord, e.g., neurofibroma, meningioma, glioma, and sarcoma.

This disclosure also provides a method of imaging the central nervous system of a subject. In some embodiments, the method can include administering to the subject a complex comprising an imaging agent associated with a carrier peptide, as described herein, and imaging the central nervous system of the subject.

The complex can be administered by any route, e.g., IV, intramuscular, SC, oral, intranasal, inhalation, transdermal, and parenteral.

The complex can be formulated with a pharmaceutically acceptable carrier selected on the basis of the selected route of administration and standard pharmaceutical practice. The complex may be formulated into dosage forms according to standard practices in the field of pharmaceutical preparations. See Alphonso Gennaro, ed., *Remington's Pharmaceutical Sciences,* 18th Edition (1990), Mack Publishing Co., Easton, Pa. Suitable dosage forms may comprise, for example, tablets, capsules, solutions, parenteral solutions, troches, suppositories, or suspensions.

For parenteral administration, the complex may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the complex. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorobutanol. The composition for parenteral administration may take the form of an aqueous or non-aqueous solution, dispersion, suspension or emulsion.

For oral administration, the complex may be combined with one or more solid inactive ingredients for the preparation of tablets, capsules, pills, powders, granules or other suitable oral dosage forms. For example, the complex may be combined with at least one excipient such as fillers, binders, humectants, disintegrating agents, solution retarders, absorption accelerators, wetting agents absorbents or lubricating agents.

The specific dose of a complex will, of course, be determined by the particular circumstances of the individual patient including the size, weight, age and sex of the patient, the nature and stage of the disease being treated, the aggressiveness of the disease disorder, and the route of administration of the compound.

Pharmaceutical Compositions

Provided herein are pharmaceutical compositions comprising a biologically active molecule or imaging agent associated with a carrier peptide. In some embodiments, the biologically active molecule or imaging agent is non-covalently bound to the carrier peptide.

The pharmaceutical compositions provided herein contain a biologically active molecule or imaging agent associated with a carrier peptide in an amount that results in transportation of the biologically active molecule or imaging agent across the blood-brain barrier, and a pharmaceutically acceptable carrier. Pharmaceutical carriers suitable for administration of the compounds provided herein include any such carriers known to those skilled in the art to be suitable for the particular mode of administration.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration and intraperitoneal injection, as well as transdermal patch preparation, dry powder inhalers, and ointments (see, e.g., Ansel Introduction to Pharmaceutical Dosage Forms, Fourth Edition 1985, 126).

The concentration of the biologically active molecule or imaging agent associated with a carrier peptide in the pharmaceutical composition will depend on absorption, inactivation and excretion rates of the compounds, the physicochemical characteristics of the compounds, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing a biologically active molecule or imaging agent associated with a carrier peptide in the range of 0.005% to 100% with the balance made up with a non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Kits

Also provided herein are kits. Typically, a kit includes a carrier peptide, as described previously. In some embodiments, a kit includes a carrier peptide and a biologically active molecule and/or imaging agent. In certain embodiments, a kit can include one or more delivery systems, e.g., for a biologically active molecule, imaging agent, carrier peptide, or any combination thereof, and directions for use of the kit (e.g., instructions for administering to a subject). In certain embodiments, a kit can include a biologically active molecule and/or an imaging agent, a carrier peptide, and/or a complex of a biologically active molecule or imaging agent and a carrier peptide. In some embodiments, the kit can include a carrier peptide and a label that indicates that the contents are to be administered to a subject with a biologically active molecule or imaging agent.

EXAMPLES

General
Materials:

All mice used (B6SJLF1) were female and were purchased from the Jackson Laboratories. Mice were maintained and used following an IRB-approved protocol. Bacterial β-galactosidase was purchased from Calbiochem (Catalog #345788). Human IgG and IgM were purchased from Sigma (Product Numbers I 4506 and I8260 respectively). The 4G8 monoclonal antibody (cat# SIG-39220) was purchased from Covance (Emeryville, Calif.). LDL receptor antibody was from abcam (Cat # ab30532).

All peptides were synthesized at the Mayo Proteomic Core Facility.

Preparation of Peptide-Protein Complex for Delivery in the Brain:

Required amount of the peptide and protein were mixed in a final volume of 300 μL PBS (phosphate buffered saline), and incubated at room temperature for 60 minutes. The mixture was vortexed for a few seconds, every fifteen minutes during the incubation period.

The mixture was injected intravenously as a bolus into the lumen of the femoral vein. This was accomplished using a heat pulled PE50 catheter. At the conclusion of the experiment, the mouse was euthanized with a lethal dose of sodium pentobarbital. Each mouse was perfused with 10 mL PBS. This perfusion was accomplished through the standard trans cardial method. The brain was removed from the skull and positioned to make an initial coronal slice at −2.0 mm bregma. Subsequently, 25 μm coronal sections were cut on a cryostat and placed on charged slides for staining of β-galactosidase activity.

Staining for Beta-Galactosidase Enzyme Activity:

Evaluation of β-galactosidase enzymatic activity was accomplished by an initial 15 minute fixation of the brain sections in 0.25% glutaraldehyde. The slides were washed with 3 changes of PBS for 5 minutes each and then rinsed in distilled water for 5 minutes. The brain sections were incubated in X-Gal (0.2%) working solution, pH 7.38, for 18 hours at 37° C. in covered containers. Following this incubation the sections were dehydrated and coverslips were applied.

Imaging by microSPECT:

Micro SPECT/CT experiments were conducted on a Gamma Medica X SPECT System (GE Healthcare). Human IgG (Sigma) and IgM (Sigma) were labeled to a high specific activity using the Chloramine-T method. 80 μg (500 μCi) of each immunoglobulin (corresponds to 0.53 nanomole of IgG and 0.13 nanomole of IgM assuming molecular weights of 150 Kd and 600 Kd for IgG and IgM, respectively) was mixed with 70-fold molar excess of K16ApoE (SEQ ID NO: 22) (as required for experiment) for 1 hour at room temperature and was administered in each mouse through the use of a catheter in the femoral vein. Immediately subsequent to the intravenous bolus injection, the mice were imaged every hour for a total of 6 hours. At the completion of the 6 hour time point, each mouse was euthanized and the systemic blood supply was transcardially perfused with 10 mL phosphate buffered saline, and imaged after 30 minutes.

Example 1

Delivery of Radiolabeled IgG Across the BBB

The delivery of radiolabeled IgG across the BBB in different brain regions in mice with and without the peptide $K_{16}ApoE$ (SEQ ID NO:22) was evaluated. In addition, the integrity of the BBB after delivery of IgG with $K_{16}ApoE$ (SEQ ID NO: 22) was examined. 3 μmol of $^{125}I$-IgG were mixed with varying amounts of the peptide $K_{16}ApoE$ (SEQ ID NO: 22) (0-55 μmol), and the mixture injected intravenously into the mice. $^{131}I$-IgG not complexed with the peptide was injected into the same animals at 59 minutes and allowed to circulate for 1 minute subsequent to the initial femoral vein injection of $^{125}I$-IgG+$K_{16}ApoE$ (SEQ ID NO: 22). Uptake of $^{125}I$-IgG and $^{131}I$-IgG were measured in different areas of the brain after 60 minutes.

TABLE 1

|  | IgG, 3 μmol | +ApoE, 8 μmol | +ApoE, 16 μmol | +ApoE, 32 μmol | +ApoE, 55 μmol |
|---|---|---|---|---|---|
| PS × 10⁶ (ml/g/s) | | | | | |
| Cortex | 0.13 +− 0.02 | 0.30 | 0.47 | 9.58 | 15.30 |
| Caudate | 0.09 +− 0.01 | 0.35 | 0.86 | 16.65 | 22.60 |
| Hippo | 0.17 +− 0.02 | 0.58 | 1.05 | 12.52 | 20.90 |
| Thalamus | 0.13 +− 0.02 | 0.29 | 1.37 | 19.60 | 21.00 |
| Brainstem | 0.20 +− 0.02 | 0.45 | 1.64 | 22.90 | 18.40 |
| Cerebellum | 0.15 +− 0.02 | 0.48 | 0.72 | 13.43 | 21.60 |
| Vp (ul/g) | | | | | |
| Cortex | 13.53 +− 0.98 | 21.39 | 21.22 | 16.41 | 25.59 |
| Caudate | 8.53 +− 0.52 | 14.44 | 11.67 | 12.89 | 20.10 |
| Hippo | 15.13 +− 2.35 | 17.49 | 16.95 | 12.67 | 21.83 |
| Thalamus | 13.79 +− 1.09 | 19.96 | 21.00 | 18.34 | 26.92 |
| Brainstem | 22.32 +− 1.51 | 19.02 | 31.50 | 20.54 | 34.60 |
| Cerebellum | 20.79 +− 1.24 | 21.28 | 23.74 | 19.79 | 24.31 |
| N (no of mice) | 4 | 2 | 2 | 2 | 1 |

PS values reflect the amount of $^{125}I$-IgG that has crossed the BBB, whereas Vp values indicate the amount of $^{131}I$-IgG at the BBB but which has not crossed the BBB.

As shown in Table 1, the PS values with IgG alone are very small for all the brain regions, indicating very little transport of the IgG across the BBB. However, the values increased significantly (~100-fold at 55 μmol of $K_{16}ApoE$ (SEQ ID NO: 22)) with increasing amounts of the delivery peptide.

On the other hand, the Vp values remained virtually unchanged in all the brain regions examined, indicating $^{131}I$-IgG failed to cross the BBB (since it was not complexed with the peptide), and attesting to the notion that the BBB was not damaged due to prior exposure to the peptide (during delivery of $^{125}I$-IgG complexed with $K_{16}ApoE$ (SEQ ID NO: 22)).

Example 2

Delivery of Alexa-IgG Assisted by $K_{16}ApoE$ (SEQ ID NO: 22) into Brain

In this experiment, AlexaIgG488 was injected into mice with or without mixing with $K_{16}ApoE$ peptide (SEQ ID NO:22). Brain sections were made 1 hour after delivery. As shown in FIG. 1, the complexed agent shows significantly brighter contrast and enhancement of brain structures compared to the uncomplexed AlexaIgG488.

Example 3

Delivery of ApoE Peptide (without $K_{16}$ Moiety (SEQ ID NO: 4)) Across the BBB and Binding of Peptide to LDL Receptors The experiments will evaluate the ApoE peptide (without the $K_{16}$ moiety (SEQ ID NO: 4)) crossing of the BBB and whether it will bind/localize to LDL receptors (LDLR) expressed in the brain. An FITC-labeled ApoE peptide will be synthesized and injected into mice. Brain specimens will be collected after 1 hour following injection, and slides will be prepared with brain sections of 10 microns thickness. The slides will be stained with antibody against LDLR and evaluated to determine whether the signals for LDLR and the ApoE peptide are co-localized.

Example 4

Location of K$_{16}$ApoE (SEQ ID NO: 22) Following Delivery Across the BBB

The experiments will determine the location of protein delivery by the carrier peptide (K$_{16}$ApoE (SEQ ID NO: 22)) within the brain. K$_{16}$ApoE (e.g., SEQ ID NO: 22)+Alexa-IgG (green fluorescence) conjugate will be prepared by mixing solutions of each at the desired concentrations and incubating the mixture at room temp for 30 minutes. The complex will be injected into mice and brain specimens collected after 1 hour. Slides will be prepared as above, and immunostained for GFAP, calbindin and neuregulin. If co-localization of IgG and GFAP is seen, such a result may indicate that the delivered IgG reached the astrocytes. Co-localization of IgG and calbindin or neuregulin, however, may indicate that the delivered IgG reached the neurons.

Example 5

Compromised Integrity of the BBB by K$_{16}$ApoE (SEQ ID NO: 22)

These experiments will evaluate whether the K$_{16}$ApoE (e.g., SEQ ID NO:22), alone or following formation of a complex, compromises the integrity of the BBB. A complex with K$_{16}$ApoE (SEQ ID NO: 22)+AlexaRedIgG will be prepared and injected into mice. After 1 hour uncomplexed AlexaGreenIgG will be injected. Brain specimens will be collected 1 hour after the second injection, and slides will be prepared using 10 micron sections. The sections will be visualized using confocal microscopy. In other mice, the reverse the experimental approach will be implemented using AlexaGreenIgG complexed with K$_{16}$ApoE (SEQ ID NO: 22) and uncomplexed AlexaRedIgG. If the peptide does not compromise the BBB, then only red fluorescence will be seen in cells in the brain. However, if the peptide does compromise the BBB, then both red and green fluorescence will be seen, and vice versa.

Example 6

Evaluation of microSPECT

A microSPECT machine can image and quantify radioactivity in various tissues in live animals under anesthesia. If K$_{16}$ApoE (SEQ ID NO: 22) indeed carries a protein (radioactive) across the BBB, then there should be more radioactivity in the brain of a mice injected with such a peptide-protein complex than in the brain of a mice injected with the radioactive protein alone.

IgG 4.1 (an antibody against the amyloid precursor protein (APP)) was radioiodinated. IgG4.1 alone or previously complexed with K$_{16}$ApoE (SEQ ID NO:22) was injected in a number of mice. The mice were anesthesized and the brain was imaged with a microSPECT machine at 1 hour intervals. Perfusion was done for some mice after six hours of quantitative imaging followed by imaging after 30 minutes.

Figure 2:
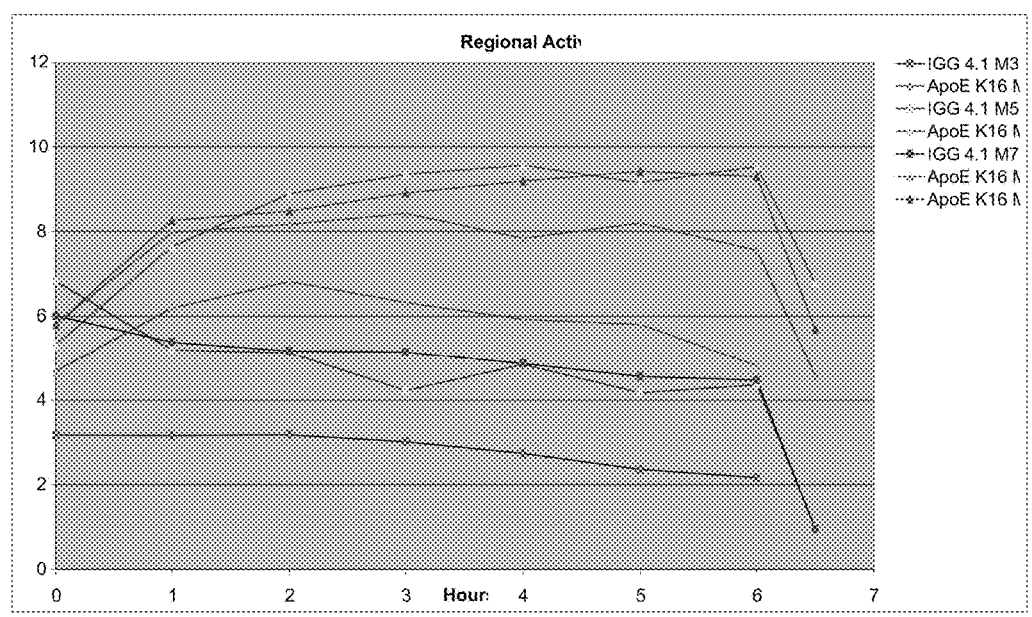
FIG. 2 illustrates the accumulation of radioactive IgG 4.1 in mouse brain aided by K$_{16}$ApoE (SEQ ID NO: 22).

The radioactivity measured at each time point for each mice was plotted against time (FIG. 2). Seven animals were used in total, they were numbered M3-M9. M3 and M4 mice were not perfused. Two mice (M5 and M7) receiving IgG 4.1 were perfused after 6 hours of imaging, and three mice (M6, M8 and M9) receiving the IgG complexed with the delivery peptide were perfused after 6 hours of imaging followed by imaging at 6.5 hours.

It is clear from the data presented in FIG. 2 that ~2-fold more radioactivity was registered in the brains of mice delivered with the IgG complexed with the peptide than the IgG alone. This difference increased to nearly 5-fold when the animals were perfused.

Radioactivity in the brains of mice receiving IgG alone indicated IgG molecules were retained in the capillaries. Increased accumulation of radioactivity in the brains of mice receiving the IgG complexed with the delivery peptide indicated IgGs were present in the capillaries as well as having crossed the BBB and retained in the brain. If the IgG crosses the BBB and is retained in brain cells, then perfusion of the brains should eliminate IgGs in the capillaries but IgGs that have crossed the BBB should still be retained, which is essentially seen for mice M6, M8 and M9, providing strong indication that the peptide helps carry the protein (IgG) through the BBB into the brain.

Example 7

Delivery of a Protein Across the BBB

Figure 3:
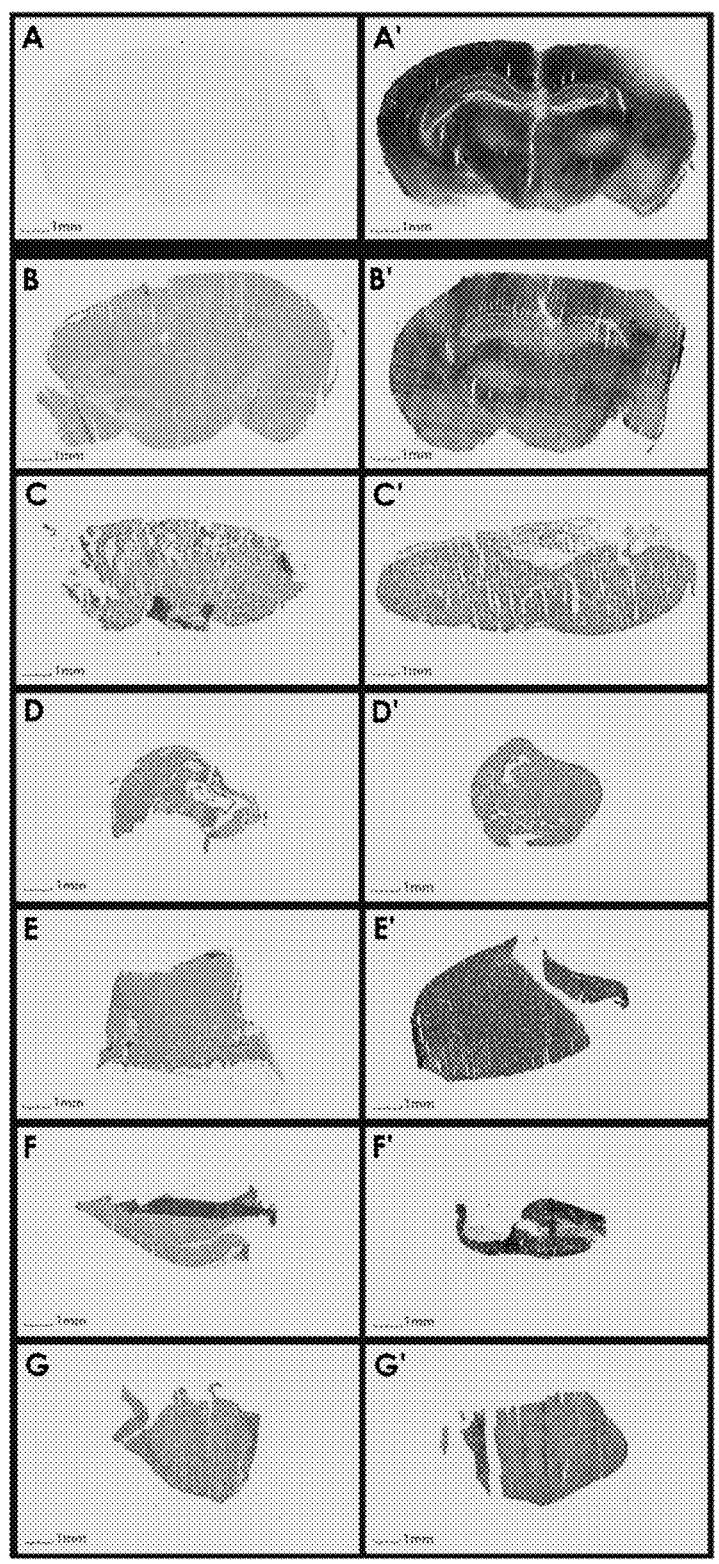
FIG. 3 shows delivery of K16ApoE-mediated (SEQ ID NO: 22) beta-galactosidase in brain (Top) and in other organs (Bottom). In one experiment, beta-galactosidase was injected in mice mixed with (FIG. 3A') and without K16ApoE (SEQ ID NO: 22) (FIG. 3A), brain slices made six hours after injection were stained for enzyme activity (top). In a separate related experiment, slides were made from different organs and stained for beta-galactosidase activity after delivery without (FIG. 3B-G) and with K16ApoE (SEQ ID NO: 22) (FIG. 3B'-G'), B-brain; C-heart, D-kidney, E-lung, F-liver, G-spleen.

To evaluate the potential of K16ApoE (SEQ ID NO: 22) for delivering a protein across the BBB, the enzyme β-galactosidase was injected in mice with or without prior mixing with K16ApoE (SEQ ID NO: 22) (at a protein to peptide molar ratio of 1:70). The experiment was repeated more than a dozen times. In this series of experiments, intense β-galactosidase activity was observed in mice brain when the enzyme-peptide mix was injected and brain slices were prepared for enzyme activity staining 6 hours after injection, whereas no activity was seen when the enzyme was injected alone (FIG. 3A). High-magnification scans of the images of β-galactosidase-stained sections in the brain showed that the enzyme was delivered in virtually every area of the brain, and stained both astrocytes and neurons, however, pyramidal cells in the hippocampus showed much weaker staining for β-galactosidase activity compared to cells in other areas of the brain. The weak β-galactosidase activity staining in the pyramidal cells does not appear to be due to low expression of LDLR in mouse hippocampus since cells in this region display strong immunohistochemical staining for the receptor. It is speculated that either X-gal or 5-bromo-4-chloroindole or both somehow leach out of this region faster than other regions of the brain resulting to a faint signal for β-galactosidase activity.

To assess if the delivery of β-galactosidase in the brain via K16ApoE (SEQ ID NO: 22) is LDLR-mediated, β-galactosidase staining in liver, brain, kidney, heart and lung after injection of the enzyme with and without mixing with K16ApoE (SEQ ID NO: 22) was also evaluated. The most intense staining was observed in liver and brain, followed by staining in lung, heart and kidney (FIG. 3B-G). This pattern of uptake of beta-galactosidase by K16ApoE (SEQ ID NO: 22) in various organs approximately follows the pattern of reported LDLR expression pattern suggesting that delivery of β-galactosidase through K16ApoE (SEQ ID NO: 22) is LDLR-mediated.

Example 8

Delivery of IgG and IgM using K16ApoE (SEQ ID NO: 22)

Figure 4:
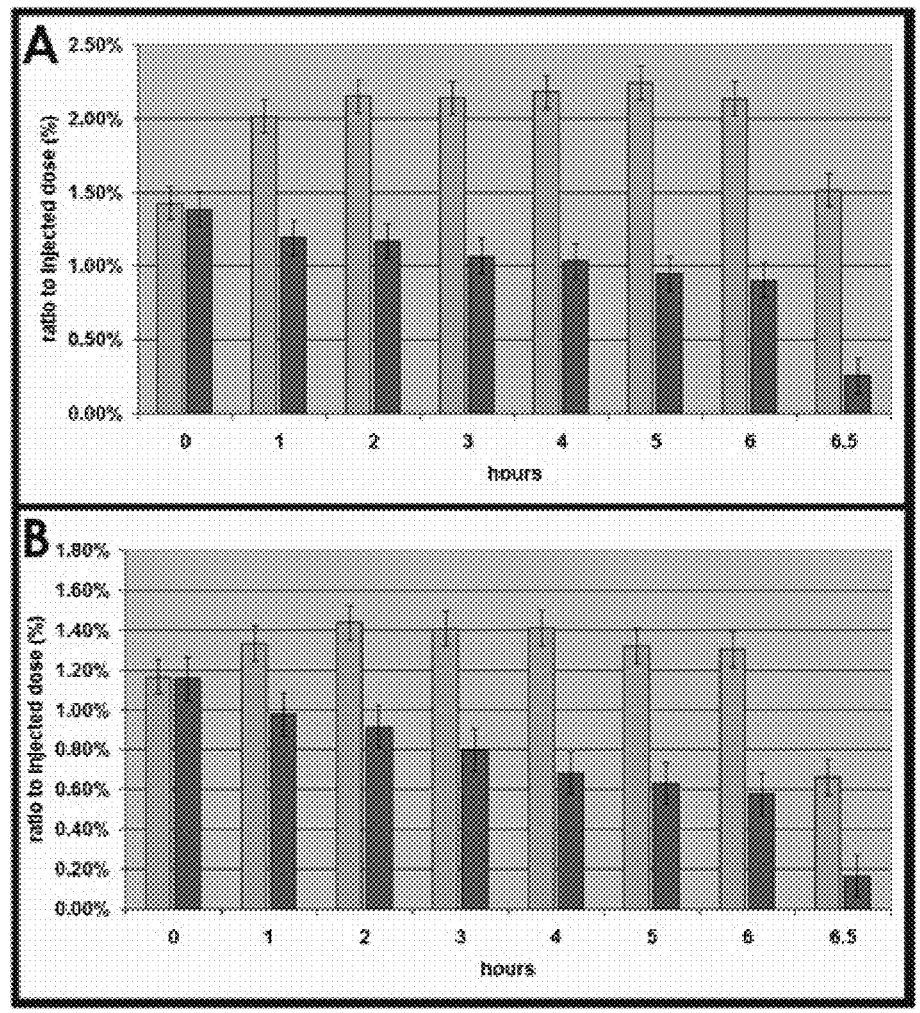
FIG. 4 shows the evaluation of K16ApoE-mediated (SEQ ID NO: 22) delivery of IgG (A) and IgM (B) in mice brains by microSPECT. Imaging was done at 1 hour intervals up to six hours, after which cardiac perfusion was performed, and final imaging carried out 30 minutes after perfusion. Left bars—with K16ApoE (SEQ ID NO: 22); Right bars—no K16ApoE (SEQ ID NO: 22).

Since many potentially therapeutic proteins against brain-associated disorders are immunoglobulins, delivery of IgG and IgM through K16ApoE (SEQ ID NO: 22) in mouse brain was evaluated by micro-single photon emission computed tomography (microSPECT) imaging. For this, radioiodinated human IgG (Sigma, product # I 4506) and human IgM (Sigma, product # I 8260) were mixed with K16ApoE (SEQ ID NO: 22) and injected intravenously. Anesthetized animals were then subjected to imaging for 6 hours at 1 hour interval. Cardiac perfusion was then performed, after which final imaging was done at 30 minutes post-perfusion. Results from these experiments provide a number of indications (FIG. 4): First, it appears that peak delivery of both IgG and IgM into brain happens around 2 hours post-injection of the peptide-protein mix, after which uptake of the proteins in the brain remains relatively unchanged up to 6 hours (maximum time point tested). Second, cardiac perfusion appears to remove most of the radioactive protein in the vasculature, concomitantly increasing the difference between apparent brain-uptake of the protein with and without the carrier peptide (~5-fold). Finally, the results suggest that about 1% of the injected immunoglobulins are transported into the brain by K16ApoE (SEQ ID NO: 22) under the experimental condition. It is interesting to note that the extent of delivery of the radiolabeled IgG and IgM into kidney, liver/spleen and heart remained virtually unchanged irrespective of whether the proteins were delivered with or without the carrier peptide. Cardiac perfusion also did not change the accumulation of radioactivity in these organs, implying that transport of proteins in these organs does not depend upon crossing of a biological barrier.

Example 9

Efficacy of Delivered Therapeutic

Figure 5:
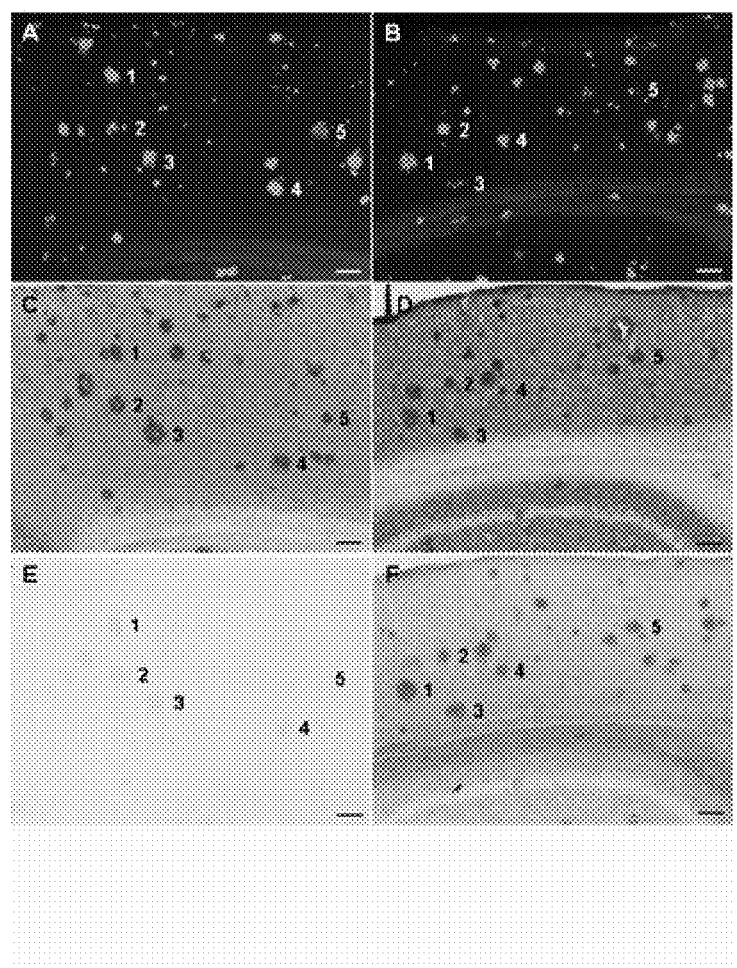
FIG. 5 illustrates labeling of amyloid plaques with a plaque-specific antibody delivered via K16ApoE (SEQ ID NO: 22) in brains of mice models of Alzheimer's disease. Two mice with Alzheimer's disease were used: one represented by A, C and E, while the other is represented by B, D and F. A, C and E represent adjacent brain sections from one mouse, whereas B, D and F represent adjacent brain sections from another mouse. A, B—thioflavine S staining; C, D—immunostaining to identify plaques using the 4G8 as the primary antibody, and an anti-mouse antibody as the secondary antibody; E, F—immunostaining using the secondary antibody only. The 4G8 IgG was injected in the first mouse (left panel) without K16ApoE (SEQ ID NO: 22), while the second mouse (right panel) received injection of the IgG mixed with K16ApoE (SEQ ID NO: 22).

For its activity, β-galactosidase does not need to bind with any molecular entity in the brain. However, for all therapeutic purposes, the delivered molecule in the brain must be able to recognize and bind with its cognate target molecule. To test this premise, an antibody against amyloid beta peptide (4G8 from Cavance) was delivered via K16ApoE (SEQ ID NO: 22) in the brains of mice which model for Alzheimer's disease. This antibody is known to recognize amyloid beta plaques. The results indicate that the antibody delivered in this manner labeled the amyloid plaques in the brain of these mice as well as identified the plaques with the antibody through standard immunohistochemistry (FIG. 5). Similar results were also obtained with another antibody (4.1 IgG, 32) known to label these plaques.

Example 10

Transportation of Protein without Damage to BBB

Figure 6:
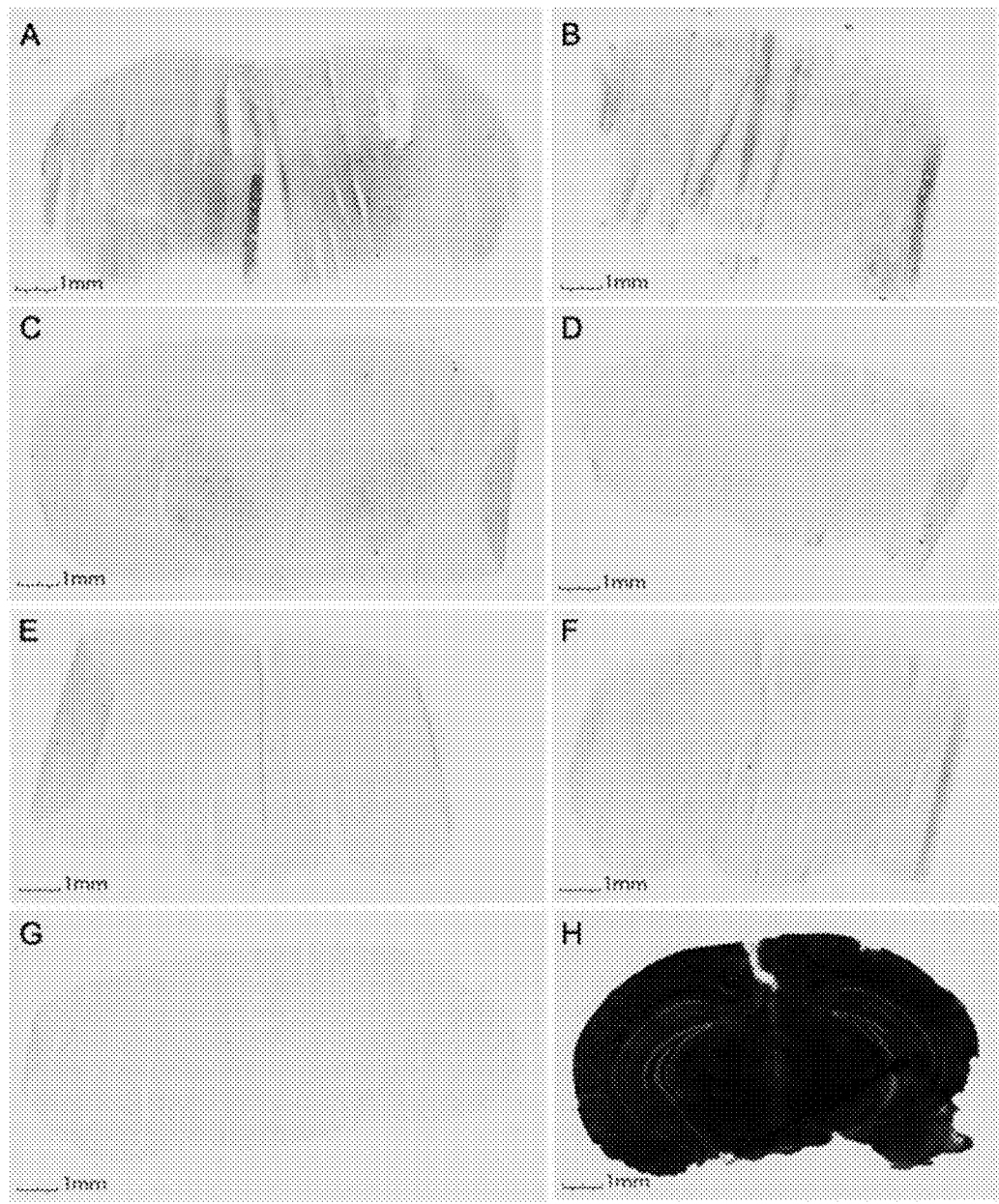
FIG. 6 shows the evaluation of the integrity of the BBB after injection of K16ApoE (SEQ ID NO: 22). Each mouse (represented by A through G) received an injection of K16ApoE (SEQ ID NO: 22), followed by injection of β-galactosidase at the indicated times. Brain slices were made 4 hours after β-galactosidase injection and were followed by staining for activity of the enzyme. A—β-galactosidase was injected 1 minute after K16ApoE (SEQ ID NO: 22) injection. B—β-galactosidase was injected 5 minutes after K16ApoE (SEQ ID NO: 22) injection. C—β-galactosidase was injected 10 minutes after K16ApoE (SEQ ID NO: 22) injection. D—β-galactosidase was injected 30 minutes after K16ApoE (SEQ ID NO: 22) injection. E—β-galactosidase was injected 1 hour after K16ApoE (SEQ ID NO: 22) injection. F—β-galactosidase was injected 2 hours after K16ApoE (SEQ ID NO: 22) injection. G—β-galactosidase was injected 4 hours after K16ApoE (SEQ ID NO: 22) injection. H—positive control (β-galactosidase mixed with K16ApoE (SEQ ID NO: 22) was injected, brain slices were made 4 hours after the injection and proceeded for staining for enzyme activity).

A transporter that efficiently carries a protein in the brain should not do so by impairing the integrity of the BBB. To evaluate if K16ApoE (SEQ ID NO: 22) impairs the integrity of the BBB, the peptide was first injected intravenously, then injected β-galactosidase at different time intervals. The control mice received the enzyme mixed with the peptide. Mice were perfused and sacrificed 6 hours after β-galactosidase injection, brain slices were made and prepared for β-galactosidase staining. Results presented in FIG. 6 show increasingly weaker β-galactosidase activity in the brains of mice receiving β-galactosidase at 1, 5 and 10 minutes after injection of K16ApoE (SEQ ID NO: 22) and no visible staining thereafter. These results indicate that most of the injected K16ApoE (SEQ ID NO: 22) becomes bound with proteins and cells in the circulation, and this binding becomes virtually complete within 10 minutes after which no free K16APoE (SEQ ID NO: 22) remains in circulation. Free K16ApoE (SEQ ID NO: 22) that remains at early time points becomes bound with beta-galactosidase and carries the enzyme in the brain. The peptide by itself and/or being bound with blood proteins/cells did not seem to affect the BBB as no β-galactosidase enzyme activity was seen in the brain from 10 min to 4 hours.

Example 11

Figure 7:
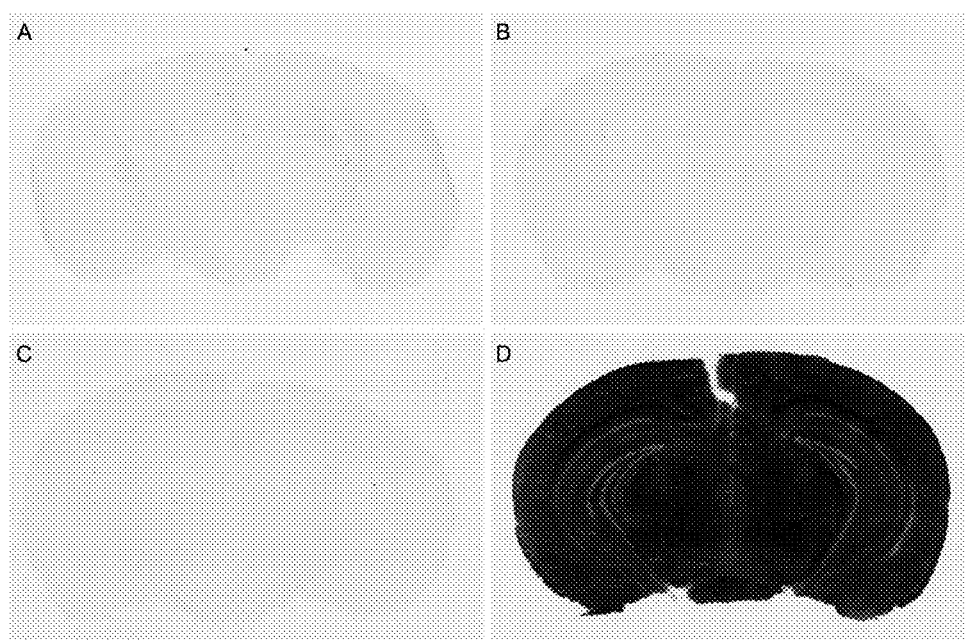
FIG. 7 demonstrates the need for chemical linking of the K16 (SEQ ID NO: 4) and the ApoE peptide moieties for non-covalent delivery across the BBB. Delivery of β-galactosidase in brain with K16 peptide (SEQ ID NO: 4) alone (A), with ApoE peptide only (B), with K16 peptide (SEQ ID NO: 4)+ApoE peptide (C), and with K16APoE peptide (SEQ ID NO: 22) (D).

Necessity of Covalent Linking of Hydrophillic Amino Acid Chain and Carrier Peptide The necessity of covalent linking of the K16 (SEQ ID NO: 4) and ApoE (SEQ ID NO: 13) peptide moieties was evaluated for non-covalent transport of a protein across the BBB. For this, β-galactosidase was mixed with either the ApoE peptide, the peptide K16 (SEQ ID NO: 4), ApoE plus K16 (SEQ ID NO: 4) or with K16ApoE (SEQ ID NO: 22), and injected in mice. Brain sections from these mice show β-galactosidase staining only in slides from mice receiving β-galactosidase mixed with K16ApoE (SEQ ID NO: 22), indicating that linking of the K16 (SEQ ID NO: 4) and the ApoE peptide moieties is critical for transport of a protein in a non-covalent manner (FIG. 7).

Example 12

Figure 8:
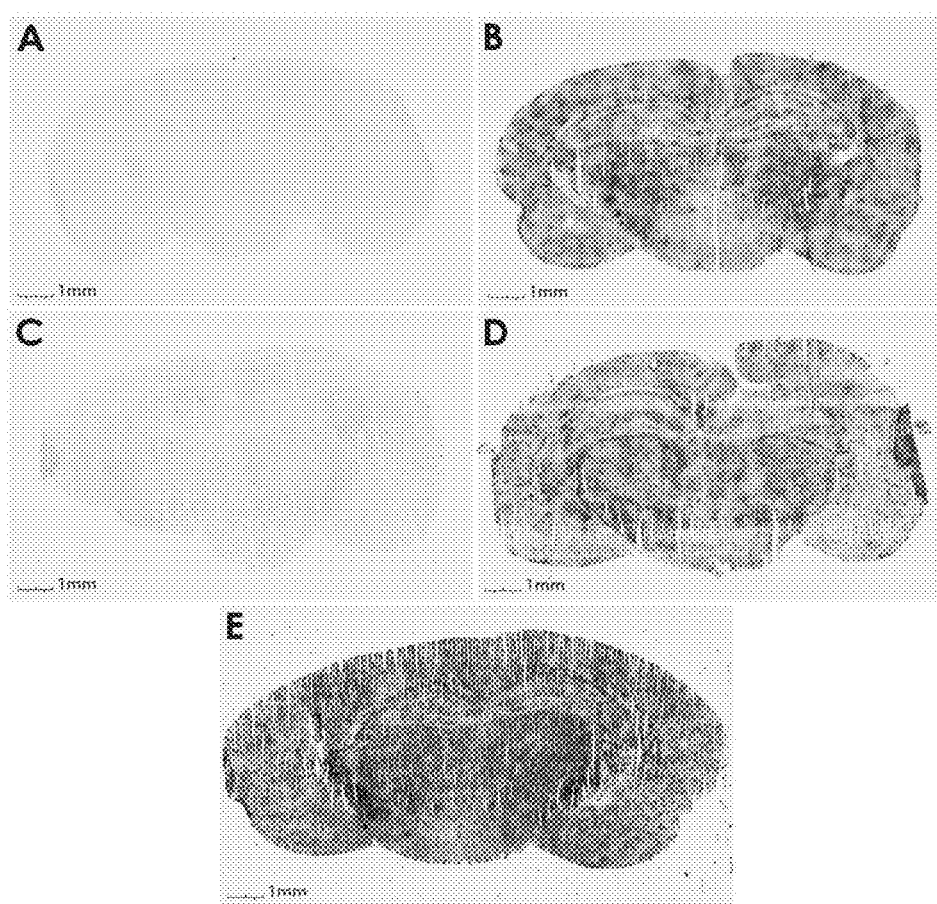
FIG. 8 illustrates the testing mutant ApoE peptides for their potential as non-covalent transporters of proteins across the BBB. A—no peptide, no β-gal; B—K16ApoE (SEQ ID NO: 22)+β-gal; C—K16L3N7 (SEQ ID NO: 126)+β-gal; D—K16L3L20 (SEQ ID NO: 127)+β-gal; E—K16N7L20 (SEQ ID NO: 128)+β-gal.

Testing Mutant ApoE Peptides for their Potential as Non-Covalent Transporters of Proteins Across the BBB β-galactosidase was mixed with equal amounts of various peptide transporters and injected into mice. Slides were prepared using 25 μm sections of the mice brains one hour after injection followed by development of enzyme staining (FIG. 8). The following peptides were evaluated:

```
                                           (SEQ ID NO: 126)
A: KKKK KKKK KKKK KKKK LRLR LANH LRKL RKRL
   LRDA;

(SEQ ID NO: 127)
B: KKKK KKKK KKKK KKKK LRLR LASH LRKL RKRL
   LRDL;

(SEQ ID NO: 128)
C: KKKK KKKK KKKK KKKK LRVR LANH LRKL RKRL
   LRDL.
```

As shown in FIG. 8, mutant A was worse than the wild-type ApoE blood-brain barrier agent, while mutants B and C were able to transport the β-galactosidase at least as well as wild-type or better.

Example 13

Time Course for β-Galactosidase Delivery in Mouse Brain with K16ApoE (SEQ ID NO: 22)

Figure 9:
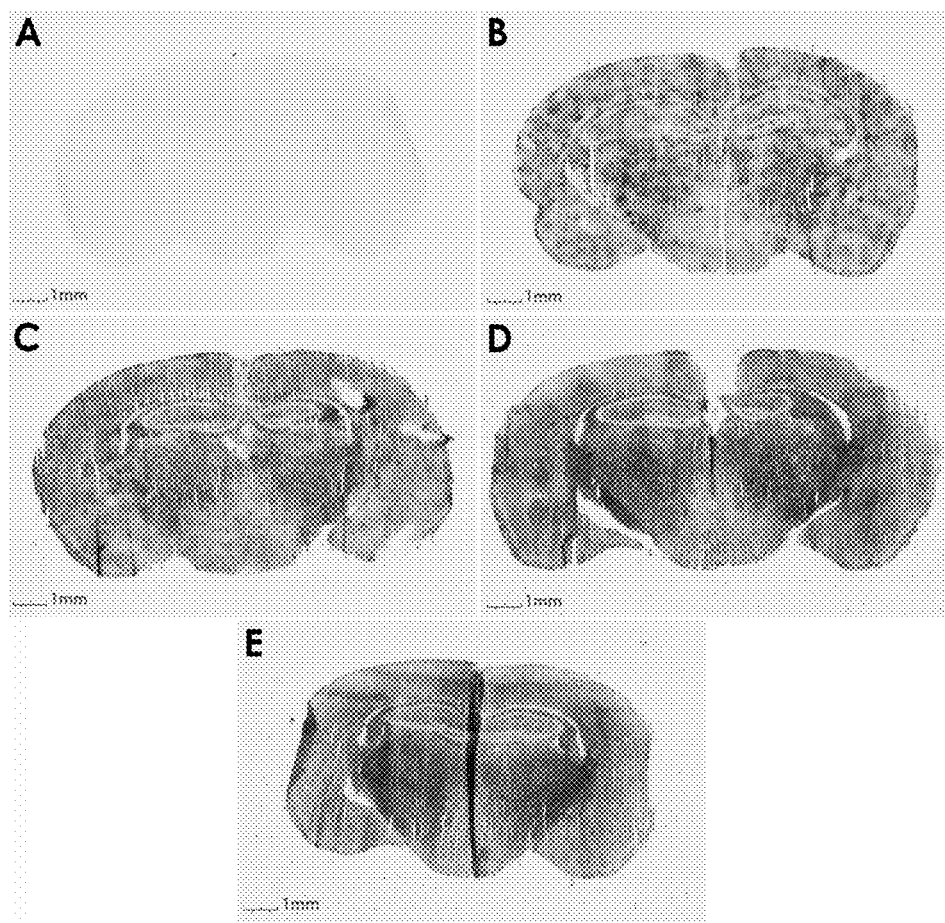
FIG. 9 shows a time course study of β-galactosidase delivery in mouse brain with K16ApoE (SEQ ID NO: 22). A—β-galactosidase, no peptide, 6 h; B—β-galactosidase+ peptide, 1 h; C—β-galactosidase+ peptide, 2 h; D—β-galactosidase+ peptide, 5 h; E—β-galactosidase+ peptide, 10 h.

In each mouse, 1.38 nanomoles of β-galactosidase was mixed with 89 nanomoles of K16ApoE (SEQ ID NO: 22) and injected intravenously. 25 μm brain slices were prepared for staining for β-galactosidase activity at indicated time points (FIG. 9).

FIG. 8 provides the following time points:
A—Beta-galactosidase, no peptide, 6 h.
B—Beta-galactosidase+ peptide, 1 h.
C—Beta-galactosidase+ peptide, 2 h.
D—Beta-galactosidase+ peptide, 5 h.
E—Beta-galactosidase+ peptide, 10 h.

A number of embodiments of the invention have been described. Nevertheless, it will be understood that various modifications may be made without departing from the spirit and scope of the invention. Accordingly, other embodiments are within the scope of the following claims.

What is claimed is:

1. A complex, or a pharmaceutically acceptable salt thereof, comprising a biologically active molecule or an imaging agent associated with a carrier peptide, wherein the carrier peptide comprises the sequence:

(SEQ ID NO: 143)
[X]n-
L-R-X1-R-X2-X3-X4-H-L-R-X5-X6-X7-K-R-L-X8-R-D-X9 wherein:
X is lysine;
n is an integer from 4 to 20;
X1 is selected from the group consisting of A, L, S, and V;
X2 is selected from the group consisting of L and M;
X3 is selected from the group consisting of A and S;
X4 is selected from the group consisting of N, S, and T;
X5 is selected from the group consisting of K and N;
X6 is selected from the group consisting of L, M, and V;
X7 is selected from the group consisting of R and P;
X8 is selected from the group consisting of L and M; and
X9 is selected from the group consisting of A and L; and
wherein the biologically active molecule is chosen from a polypeptide; small molecule; antibody; antibody fragment; carbohydrate; polysaccharide; lipid; glycolipid; antigen; and antigenic peptide.

2. The complex of claim 1, wherein the carrier peptide is selected from the group consisting of:

(SEQ ID NO: 19)
K-K-K-K-L-R-V-R-L-A-S-H-L-R-K-L-R-K-R-L-L-R-D-A;

(SEQ ID NO: 20)
K-K-K-K-K-K-K-L-R-V-R-L-A-S-H-L-R-K-L-R-K-R-L-L-R-D-A;

(SEQ ID NO: 21)
K-K-K-K-K-K-K-K-K-K-L-R-V-R-L-A-S-H-L-R-K-L-R-K-R-L-L-R-D-A;

(SEQ ID NO: 22)
K-K-K-K-K-K-K-K-K-K-K-K-K-L-R-V-R-L-A-S-H-L-R-K-L-R-K-R-L-L-R-D-A;

(SEQ ID NO: 23)
K-K-K-K-K-K-K-K-K-K-K-K-K-K-K-K-K-L-R-V-R-L-A-S-H-L-R-K-L-R-K-R-L-L-R-D-A;

(SEQ ID NO: 46)
K-K-K-K-L-R-S-R-L-A-S-H-L-R-K-L-R-K-R-L-L-R-D-A;

(SEQ ID NO: 47)
K-K-K-K-K-K-K-L-R-S-R-L-A-S-H-L-R-K-L-R-K-R-L-L-R-D-A;

-continued (SEQ ID NO: 48)
K-K-K-K-K-K-K-K-K-K-L-R-S-R-L-A-S-H-L-R-K-L-R-K-R-L-L-R-D-A;

(SEQ ID NO: 49)
K-K-K-K-K-K-K-K-K-K-K-K-K-L-R-S-R-L-A-S-H-L-R-K-L-R-K-R-L-L-R-D-A;

(SEQ ID NO: 50)
K-K-K-K-K-K-K-K-K-K-K-K-K-K-K-K-K-L-R-S-R-L-A-S-H-L-R-K-L-R-K-R-L-L-R-D-A;

(SEQ ID NO: 51)
K-K-K-K-L-R-V-R-M-A-S-H-L-R-K-L-R-K-R-L-L-R-D-A;

(SEQ ID NO: 52)
K-K-K-K-K-K-L-R-V-R-M-A-S-H-L-R-K-L-R-K-R-L-L-R-D-A;

(SEQ ID NO: 53)
K-K-K-K-K-K-K-K-K-K-L-R-V-R-M-A-S-H-L-R-K-L-R-K-R-L-L-R-D-A;

(SEQ ID NO: 54)
K-K-K-K-K-K-K-K-K-K-K-K-K-L-R-V-R-M-A-S-H-L-R-K-L-R-K-R-L-L-R-D-A;

(SEQ ID NO: 55)
K-K-K-K-K-K-K-K-K-K-K-K-K-K-K-K-K-L-R-V-R-M-A-S-H-L-R-K-L-R-K-R-L-L-R-D-A;

(SEQ ID NO: 56)
K-K-K-K-L-R-V-R-L-A-T-H-L-R-K-L-R-K-R-L-L-R-D-A;

(SEQ ID NO: 57)
K-K-K-K-K-K-K-L-R-V-R-L-A-T-H-L-R-K-L-R-K-R-L-L-R-D-A;

(SEQ ID NO: 58)
K-K-K-K-K-K-K-K-K-K-L-R-V-R-L-A-T-H-L-R-K-L-R-K-R-L-L-R-D-A;

(SEQ ID NO: 59)
K-K-K-K-K-K-K-K-K-K-K-K-K-L-R-V-R-L-A-T-H-L-R-K-L-R-K-R-L-L-R-D-A;

(SEQ ID NO: 60)
K-K-K-K-K-K-K-K-K-K-K-K-K-K-K-K-K-L-R-V-R-L-A-T-H-L-R-K-L-R-K-R-L-L-R-D-A;

(SEQ ID NO: 61)
K-K-K-L-R-V-R-L-A-S-H-L-R-K-L-P-K-R-L-L-R-D-A;

(SEQ ID NO: 62)
K-K-K-K-K-K-L-R-V-R-L-A-S-H-L-R-K-L-P-K-R-L-L-R-D-A;

(SEQ ID NO: 63)
K-K-K-K-K-K-K-K-K-K-L-R-V-R-L-A-S-H-L-R-K-L-P-K-R-L-L-R-D-A;

(SEQ ID NO: 64)
K-K-K-K-K-K-K-K-K-K-K-K-K-L-R-V-R-L-A-S-H-L-R-K-L-P-K-R-L-L-R-D-A;

(SEQ ID NO: 65)
K-K-K-K-K-K-K-K-K-K-K-K-K-K-K-K-K-L-R-V-R-L-A-S-H-L-R-K-L-P-K-R-L-L-R-D-A;

(SEQ ID NO: 66)
K-K-K-L-R-V-R-L-A-S-H-L-R-K-L-R-K-R-L-M-R-D-A;

(SEQ ID NO: 67)
K-K-K-K-K-K-L-R-V-R-L-A-S-H-L-R-K-L-R-K-R-L-M-R-D-A;

(SEQ ID NO: 68)
K-K-K-K-K-K-K-K-K-K-L-R-V-R-L-A-S-H-L-R-K-L-R-K-R-L-M-R-D-A;

```
                                                      (SEQ ID NO: 69)
K-K-K-K-K-K-K-K-K-K-K-K-K-K-L-R-V-R-L-A-S-H-L-R-K-L-R-K-R-L-M-R-
D-A;

(SEQ ID NO: 70)
K-K-K-K-K-K-K-K-K-K-K-K-K-K-K-K-K-L-R-V-R-L-A-S-H-L-R-K-L-R-K-
R-L-M-R-D-A;

(SEQ ID NO: 71)
K-K-K-K-L-R-V-R-L-A-S-H-L-R-N-L-R-K-R-L-L-R-D-A;

(SEQ ID NO: 72)
K-K-K-K-K-K-L-R-V-R-L-A-S-H-L-R-N-L-R-K-R-L-L-R-D-A;

(SEQ ID NO: 73)
K-K-K-K-K-K-K-K-K-K-L-R-V-R-L-A-S-H-L-R-N-L-R-K-R-L-L-R-D-A;

(SEQ ID NO: 74)
K-K-K-K-K-K-K-K-K-K-K-K-K-K-L-R-V-R-L-A-S-H-L-R-N-L-R-K-R-L-L-R-D-
A;

(SEQ ID NO: 75)
K-K-K-K-K-K-K-K-K-K-K-K-K-K-K-K-K-L-R-V-R-L-A-S-H-L-R-N-L-R-K-
R-L-L-R-D-A;

(SEQ ID NO: 76)
K-K-K-L-R-V-R-L-A-S-H-L-R-K-V-R-K-R-L-L-R-D-A;

(SEQ ID NO: 77)
K-K-K-K-K-K-L-R-V-R-L-A-S-H-L-R-K-V-R-K-R-L-L-R-D-A;

(SEQ ID NO: 78)
K-K-K-K-K-K-K-K-K-K-L-R-V-R-L-A-S-H-L-R-K-V-R-K-R-L-L-R-D-A;

(SEQ ID NO: 79)
K-K-K-K-K-K-K-K-K-K-K-K-K-L-R-V-R-L-A-S-H-L-R-K-V-R-K-R-L-L-R-D-
A;

(SEQ ID NO: 80)
K-K-K-K-K-K-K-K-K-K-K-K-K-K-K-K-L-R-V-R-L-A-S-H-L-R-K-V-R-K-
R-L-L-R-D-A;

(SEQ ID NO: 81)
K-K-K-L-R-V-R-M-S-S-H-L-R-K-L-R-K-R-L-L-R-D-A;

(SEQ ID NO: 82)
K-K-K-K-K-K-L-R-V-R-M-S-S-H-L-R-K-L-R-K-R-L-L-R-D-A;

(SEQ ID NO: 83)
K-K-K-K-K-K-K-K-K-K-L-R-V-R-M-S-S-H-L-R-K-L-R-K-R-L-L-R-D-A;

(SEQ ID NO: 84)
K-K-K-K-K-K-K-K-K-K-K-K-K-L-R-V-R-M-S-S-H-L-R-K-L-R-K-R-L-L-R-D-
A;

(SEQ ID NO: 85)
K-K-K-K-K-K-K-K-K-K-K-K-K-K-K-K-L-R-V-R-M-S-S-H-L-R-K-L-R-K-
R-L-L-R-D-A;

(SEQ ID NO: 86)
K-K-K-L-R-V-R-L-A-S-H-L-R-N-V-R-K-R-L-L-R-D-A;

(SEQ ID NO: 87)
K-K-K-K-K-K-L-R-V-R-L-A-S-H-L-R-N-V-R-K-R-L-L-R-D-A;

(SEQ ID NO: 88)
K-K-K-K-K-K-K-K-K-K-L-R-V-R-L-A-S-H-L-R-N-V-R-K-R-L-L-R-D-A;

(SEQ ID NO: 89)
K-K-K-K-K-K-K-K-K-K-K-K-K-L-R-V-R-L-A-S-H-L-R-N-V-R-K-R-L-L-R-D-
A;
```

```
                                               (SEQ ID NO: 90)
K-K-K-K-K-K-K-K-K-K-K-K-K-K-K-K-K-L-R-V-R-L-A-S-H-L-R-N-V-R-K-
R-L-L-R-D-A;

(SEQ ID NO: 91)
K-K-K-K-L-R-V-R-L-A-S-H-L-R-N-M-R-K-R-L-L-R-D-A;

(SEQ ID NO: 92)
K-K-K-K-K-K-L-R-V-R-L-A-S-H-L-R-N-M-R-K-R-L-L-R-D-A;

(SEQ ID NO: 93)
K-K-K-K-K-K-K-K-K-L-R-V-R-L-A-S-H-L-R-N-M-R-K-R-L-L-R-D-A;

(SEQ ID NO: 94)
K-K-K-K-K-K-K-K-K-K-K-K-L-R-V-R-L-A-S-H-L-R-N-M-R-K-R-L-L-R-
D-A;

(SEQ ID NO: 95)
K-K-K-K-K-K-K-K-K-K-K-K-K-K-K-K-K-L-R-V-R-L-A-S-H-L-R-N-M-R-K-
R-L-L-R-D-A;

(SEQ ID NO: 96)
K-K-K-L-R-A-R-M-A-S-H-L-R-K-L-R-K-R-L-L-R-D-A;

(SEQ ID NO: 97)
K-K-K-K-K-K-L-R-A-R-M-A-S-H-L-R-K-L-R-K-R-L-L-R-D-A;

(SEQ ID NO: 98)
K-K-K-K-K-K-K-K-K-L-R-A-R-M-A-S-H-L-R-K-L-R-K-R-L-L-R-D-A;

(SEQ ID NO: 99)
K-K-K-K-K-K-K-K-K-K-K-K-L-R-A-R-M-A-S-H-L-R-K-L-R-K-R-L-L-R-
D-A;

(SEQ ID NO: 100)
K-K-K-K-K-K-K-K-K-K-K-K-K-K-K-K-K-L-R-A-R-M-A-S-H-L-R-K-L-R-K-
R-L-L-R-D-A;

(SEQ ID NO: 101)
K-K-K-K-L-R-V-R-L-S-S-H-L-R-K-L-R-K-R-L-M-R-D-A;

(SEQ ID NO: 102)
K-K-K-K-K-K-L-R-V-R-L-S-S-H-L-R-K-L-R-K-R-L-M-R-D-A;

(SEQ ID NO: 103)
K-K-K-K-K-K-K-K-K-L-R-V-R-L-S-S-H-L-R-K-L-R-K-R-L-M-R-D-A;

(SEQ ID NO: 104)
K-K-K-K-K-K-K-K-K-K-K-K-L-R-V-R-L-S-S-H-L-R-K-L-R-K-R-L-M-R-D-
A;

(SEQ ID NO: 105)
K-K-K-K-K-K-K-K-K-K-K-K-K-K-K-K-K-L-R-V-R-L-S-S-H-L-R-K-L-R-K-R-
L-M-R-D-A;

(SEQ ID NO: 106)
K-K-K-L-R-S-R-L-A-S-H-L-R-K-L-R-K-R-L-M-R-D-A;

(SEQ ID NO: 107)
K-K-K-K-K-K-L-R-S-R-L-A-S-H-L-R-K-L-R-K-R-L-M-R-D-A;

(SEQ ID NO: 108)
K-K-K-K-K-K-K-K-K-L-R-S-R-L-A-S-H-L-R-K-L-R-K-R-L-M-R-D-A;

(SEQ ID NO: 109)
K-K-K-K-K-K-K-K-K-K-K-K-L-R-S-R-L-A-S-H-L-R-K-L-R-K-R-L-M-R-D-
A;

(SEQ ID NO: 110)
K-K-K-K-K-K-K-K-K-K-K-K-K-K-K-K-K-L-R-S-R-L-A-S-H-L-R-K-L-R-K-R-
L-M-R-D-A;
```

-continued

K-K-K-K-L-R-V-R-L-A-S-H-L-R-K-M-R-K-R-L-M-R-D-A; (SEQ ID NO: 116)

K-K-K-K-K-K-L-R-V-R-L-A-S-H-L-R-K-M-R-K-R-L-M-R-D-A; (SEQ ID NO: 117)

K-K-K-K-K-K-K-K-L-R-V-R-L-A-S-H-L-R-K-M-R-K-R-L-M-R-D-A; (SEQ ID NO: 118)

K-K-K-K-K-K-K-K-K-K-L-R-V-R-L-A-S-H-L-R-K-M-R-K-R-L-M-R-D-A; (SEQ ID NO: 119)

K-K-K-K-K-K-K-K-K-K-K-K-K-K-K-K-L-R-V-R-L-A-S-H-L-R-K-M-R-K-R-L-M-R-D-A; (SEQ ID NO: 120)

K-K-K-K-L-R-V-R-L-A-S-H-L-R-N-L-P-K-R-L-L-R-D-A; (SEQ ID NO: 121)

K-K-K-K-K-K-L-R-V-R-L-A-S-H-L-R-N-L-P-K-R-L-L-R-D-A; (SEQ ID NO: 122)

K-K-K-K-K-K-K-K-K-K-L-R-V-R-L-A-S-H-L-R-N-L-P-K-R-L-L-R-D-A; (SEQ ID NO: 123)

K-K-K-K-K-K-K-K-K-K-K-K-K-K-L-R-V-R-L-A-S-H-L-R-N-L-P-K-R-L-L-R-D-A; (SEQ ID NO: 124)

K-K-K-K-K-K-K-K-K-K-K-K-K-K-K-K-K-K-L-R-V-R-L-A-S-H-L-R-N-L-P-K-R-L-L-R-D-A; (SEQ ID NO: 125)

K-K-K-K-L-R-L-R-L-A-S-H-L-R-K-L-R-K-R-L-L-R-D-L; (SEQ ID NO: 131)

K-K-K-K-K-K-L-R-L-R-L-A-S-H-L-R-K-L-R-K-R-L-L-R-D-L; (SEQ ID NO: 132)

K-K-K-K-K-K-K-K-K-K-L-R-L-R-L-A-S-H-L-R-K-L-R-K-R-L-L-R-D-L; (SEQ ID NO: 133)

K-K-K-K-K-K-K-K-K-K-K-K-K-K-L-R-L-R-L-A-S-H-L-R-K-L-R-K-R-L-L-R-D-L; (SEQ ID NO: 134)

K-K-K-K-K-K-K-K-K-K-K-K-K-K-K-K-K-K-L-R-L-R-L-A-S-H-L-R-K-L-R-K-R-L-L-R-D-L; (SEQ ID NO: 135)

K-K-K-K-L-R-V-R-L-A-N-H-L-R-K-L-R-K-R-L-L-R-D-L; (SEQ ID NO: 136)

K-K-K-K-K-K-L-R-V-R-L-A-N-H-L-R-K-L-R-K-R-L-L-R-D-L; (SEQ ID NO: 137)

K-K-K-K-K-K-K-K-K-K-L-R-V-R-L-A-N-H-L-R-K-L-R-K-R-L-L-R-D-L; (SEQ ID NO: 138)

K-K-K-K-K-K-K-K-K-K-K-K-K-K-L-R-V-R-L-A-N-H-L-R-K-L-R-K-R-L-L-R-D-L; (SEQ ID NO: 139)

K-K-K-K-K-K-K-K-K-K-K-K-K-K-K-K-K-K-L-R-V-R-L-A-N-H-L-R-K-L-R-K-R-L-L-R-D-L. (SEQ ID NO: 140)

\* \* \* \* \*

UNITED STATES PATENT AND TRADEMARK OFFICE
CERTIFICATE OF CORRECTION

| | | |
|---|---|---|
| PATENT NO. | : 9,597,408 B2 | |
| APPLICATION NO. | : 14/281389 | |
| DATED | : March 21, 2017 | |
| INVENTOR(S) | : Geoffry L. Curran et al. | |

It is certified that error appears in the above-identified patent and that said Letters Patent is hereby corrected as shown below:

On the Title Page

Column 1 (Inventors), please delete "Erik" and insert -- Eric --, therefor;

In the Claims

Column 103, Line 34 (Claim 1), please delete "comprises" and insert -- consists of --, therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*